US008093025B2

(12) United States Patent
Loessner et al.

(10) Patent No.: US 8,093,025 B2
(45) Date of Patent: Jan. 10, 2012

(54) BACTERIAL VECTOR

(75) Inventors: Holger Loessner, Braunschweig (DE);
Anne Endmann, Braunschweig (DE);
Sara Leschner, Braunschweig (DE);
Siegfried Weiss, Braunschweig (DE)

(73) Assignee: Helmholtz-Zentrum fuer Infektionsforschung GmbH, Braunschweig (DE)

( * ) Notice: Subject to any disclaimer, the term of this patent is extended or adjusted under 35 U.S.C. 154(b) by 62 days.

(21) Appl. No.: 11/667,034

(22) PCT Filed: Sep. 2, 2005

(86) PCT No.: PCT/EP2005/054343
§ 371 (c)(1),
(2), (4) Date: Jul. 23, 2007

(87) PCT Pub. No.: WO2006/048344
PCT Pub. Date: May 11, 2006

(65) Prior Publication Data
US 2008/0112928 A1    May 15, 2008

(30) Foreign Application Priority Data
Nov. 5, 2004  (EP) ..................................... 04105564

(51) Int. Cl.
*C12N 13/00* (2006.01)
(52) U.S. Cl. .................. 435/172.1; 536/23.1; 536/24.1; 536/24.2; 435/91.1
(58) Field of Classification Search ........................ None
See application file for complete search history.

(56) References Cited

FOREIGN PATENT DOCUMENTS
WO      WO 99/55364      11/1999

OTHER PUBLICATIONS

Vile et al (Gene Therapy, vol. 7, pp. 2-8, 2000).*
Rochlitz C. F. (Swiss Medicine Weekly, 131:4-9, 2001).*
Verma et al, (Nature, vol. 389, No. 6648, pp. 239-242, 1997.*
Lisa M. Bowers et al,., Bacterial Expression System with Tightly Regulated Gene Expression and Plasmid Copy Number', *Gene: An International Journal on Genes and Genomes*, vol. 340, No. 1, Sep. 29, 2004, pp. 11-18.
Burkhard Wilms et al., High-Cell-Density Fermentation for Production of L-N-Carbamoylase using an Expression System Based on the *Escherichia coli* rhaBAD Promoter', *Biotechnology and Bioengineering*, vol. 73, No. 2, Apr. 20, 2001, pp. 95-103.
Sandy M. Wong et al., "Inducible Expression System and Marker-Linked Mutagenesis Approach for Functional Genomics of *Haemophilus influenzae*", *Gene: An International Journal of Genes and Genomes*, vol. 316, Oct. 16, 2003, pp. 177-186.
Siegfried Weiss et al., "Bacteria-Mediated Transfer of Eukaryotic Expression Plasmids into Mammalian Host Cells",*Biological Chemistry*, vol. 382, No. 4, Apr. 2001, pp. 533-541.
Siegfried Weiss et al., "Transfer of Eukaryotic Expression Plasmids to Mammalian Host Cells by Bacterial Carriers",*Current Opinion in Biotechnology*, vol. 12, No. 5, Oct. 2001, pp. 467-472.
Holger Loessner et al., "Bacteria-Mediated DNA Transfer in Gene Therapy and Vaccination", *Expert Opinion on Biological Therapy*, vol. 4, No. 2, Feb. 2004, pp. 157-168.
Guido Dietrich et al., "Live Attenuated Bacteria as Vectors to Deliver Plasmid DNA Vaccines", *Current Opinion in Molecular Therapeutics, Current Drugs*, vol. 5, No. 1, Feb. 2003, pp. 10-19.

* cited by examiner

*Primary Examiner* — Jennifer Graser
(74) *Attorney, Agent, or Firm* — Greer Burns & Crain, Ltd.

(57) ABSTRACT

The present invention relates to a combination of compounds for introducing nucleic acids and/or protein into animal cells, tissue, organs or organisms in vitro, extracorporal, or in vivo. This combination comprises preparations suitable for administration to an animal or human for medical purposes, comprising as one component a bacterial vector genetically manipulated to contain nucleic acid sequences comprising a transgene, and a second component for the subsequent transcription, possibly translation of the transgene by controlled induction of bacterial vector as it is present within the animal or human.

24 Claims, 4 Drawing Sheets

- CT26 tumor
- Spleen
- Liver

Figure 17 strain SL7207::HL260b[pTNFa-lux]

*( shown elements not drawn to scale )*

BACTERIAL VECTOR

The present invention relates to a combination of compounds for introducing nucleic acids and/or protein into animal cells, tissue, organs or organisms in vitro, extracorporal, or in vivo. This combination or system comprises preparations suitable for administration to an animal or human, comprising as one component a bacterial vector genetically manipulated to contain nucleic acid sequences comprising a transgene, and a second component allowing the subsequent transcription, possibly translation of the transgene by controlled induction of the transgene activity within the bacterial vector as it is present within the animal or human.

Applications of the system according to the invention are medical uses, e.g. immunization, tumor treatment, and release of pharmaceutically active compounds, e.g. hormones, immunomodulating compounds and pro-drug converting enzymes.

BACKGROUND STATE OF ART

For traditional vaccination, attenuated pathogens are in use to elicit an immune response from the recipient organism that is also active against wild type pathogens. An example for the use of attenuated invasive bacteria as a vaccine is the use of attenuated enteropathogenic salmonella, providing protection against salmonellosis.

Depending on the disease against which immunoprotection is intended, it is desired to elicit a variety of the immune responses such as the stimulation of antibody production and/or T-cell mediated immunity, systemically and/or mucosally. As the quality of these immunoreactions is at least in part dependent on the route of administration, a vector according to the invention can be designed to preferentially elicit a cellular and/or humoral immune response.

Although effective in recognising antigens and marking antigen for subsequent removal, antibodies cannot bind to intracellular antigens, for example to bacteria which are contained within the phagosome of infected cells, or to cytosolic antigens of malignant cells, i.e. tumor cells. This part of the immune response is provided by the cellular immune response, i.e. T-cells recognizing foreign peptide displayed on the outer surface of infected cells in conjunction with MHC-I and/or MHC-II complexes. However, in relation to tumor cells, the cellular immune response against these is often hampered by self-tolerance of the immune system against homologous constituents.

In general, antigen specific cytotoxic T-lymphocytes (CTL), which are one sub-group of T-cells, are activated by interaction with antigen presented on the cell surface in a complex with MHC I, which is the presentation pathway for cytosolic protein of mammalian cells. Accordingly, antigen synthesized by invasive pathogens in the cytoplasm, or antigen synthesized by bacterial vectors based on attenuated invasive bacteria which liberate antigen into the cytoplasm, is efficient in eliciting the cellular immune response by CTL. Following this activation, CTL are immediately directed against infected cells that display the relevant antigenic peptides in complex with MHC I.

Some invasive bacteria, e.g. salmonella, are able to specifically target professional antigen presenting cells (APC) in the infected organism. In the case of salmonella, the bacteria invade the mammalian organism mainly by passage through the M cells of Peyer patches within the small intestiny. Subsequent to passaging M cells, invasive bacteria infect dendritic cells and macrophages present in Peyer patches which are part of the mucosa associated lymphoid tissue. Peyer patches contain an increased number of APC of the gut associated lymphoid tissue, wherein bacteria can persist for days up to several weeks, depending on the degree of their attenuation. APC infected with salmonella can migrate into mesenteric lymph nodes, spleen and liver, effectively transporting invaded bacteria into these tissues. Macrophages which are lysed after infection by invasive bacteria are phagocytosed by dendritic cells.

Some invasive bacteria, e.g. salmonella, are able to replicate within the phagosome of mammalian cells, e.g. macrophages, by secreting a range of proteins and further effector molecules. These secreted molecules for example prohibit the import of NADPH oxidase into the phagosome, effectively preventing an immediate antibacterial response by the macrophages. As a further result of the infection with salmonella, caspase 1 is activated, leading to the secretion of inflammatory cytokines (IL-1 beta, IL-18) and initiating apoptosis of infected cells. Material of apoptotic macrophages which are phagocytosed by dendritic cells enter the presentation pathway of MHC I and MHC II, in turn initiating specific T-cell responses.

Some invasive bacteria, e.g. *Listeria monocytogenes* and *Shigella* spp., are able to replicate within the cytoplasm of mammalian cells. Upon lysis, the bacterial content can be released directly into the cytosol of infected cells, providing access to the MHC-I presentation pathway.

It is known that bacterial vaccine strains can induce mucosal and systemic immune responses, e.g. Salmonella administered orally.

Attracted by the efficiency of invasive bacteria to elicit an immune response, attenuated invasive bacteria have been investigated to serve as bacterial vectors for vaccines eliciting an immune response against a peptide foreign to the bacterial vector.

In addition, attenuated invasive bacteria have been used for genetic vaccination and gene therapeutic purposes as carrier vehicles to introduce eukaryotic expression plasmids into mammalian cells. In order to allow transcription of DNA sequences introduced into a mammalian cell, the DNA needs to be transported into the cellular nucleus. One prerequisite for efficient DNA transfer is an efficient invasion of host cells by the bacterial carrier vehicle. After invasion of the host cell, lysis of the bacterial vector to release its contents into the cytoplasm and a subsequent effective translocation of DNA into the nucleus are essential steps for transcription of the eukaryotic expression plasmid.

When using attenuated invasive bacteria as bacterial vectors for the transfer of protein and/or nucleic acid into mammalian cells, it is desirable to control the level of expression of said peptide and/or the copy number of nucleic acids. Up to now most attempts to control the expression of a foreign peptide by bacterial vectors rely on constitutive promoter sequences. Recently, also in vivo inducible promoters isolated from invasive bacteria, e.g. Salmonella, and have been used for this purpose. These promoters are regulated depending on the stage of the infectious cycle of said bacteria. Accordingly, such promoter sequences automatically respond to specific phases of the infectious cycle of the bacterium, so that they cannot be regulated by exerting an external influence. For example, Dunstan et al. (*Infection and Immunity*, October 1999, pages 5133 to 5141) disclose construction and analysis of expression plasmids for use in the known attenuated vaccine strain *Salmonella enterica* serovar Typhimurium ΔaroAD as the bacterial vector for a vaccine. The promoter elements were arranged before the structural gene for the C-terminal fragment of the tetanus toxin and luciferase, respectively. The in vivo induction to the promoter elements originating from salmonella and *E. coli* depends on environmental factors that naturally occur during the infectious cycle. For example, the promoter pagC is induced within the phagosomal compartment of eucaryotic cells as a result of their low concentrations of $Mg^{2+}$.

Dietrich et al. (Current Opinion in Molecular Therapeutics 5, 1, pages 10-19 (2003)) discuss the release of DNA from *Listeria monocytogenes* by an active lytic process, achieved by lysis of intracellular bacteria by treatment with antibiotics or, alternatively, by dedicated autolysis of the vector organism. For dedicated autolysis, the Listeria-specific phage lysin gene is suggested for expression under control of a listerial promoter, which is activated upon escape of the bacteria from the host cell phagosome into the cytosol. However, induction of this promoter regulating the lysis gene is only dependent upon the environment of the vector, whereas a control from outside the bacterial vector, i.e. arbitrarily, is impossible.

Jain et al. (Infection and Immunity, 986-989 (2000)) report the expression of lysis genes S and R from page lambda in gram-negative bacteria under the control of an L-arabinose inducible promoter in vitro.

However, in the state of art presently known to the inventors, no hint or assumption can be found that a saccharide inducible promoter functionally linked to a transgene, contained within a bacterial vector by genetic modification, can be controlled by applying a stimulus to an animal that has been treated by administration of the bacterial vector. In detail, the state of art does not suggest that induction of a transgene may be controlled under circumstances where the inductor cannot be delivered to the bacterial vector directly, i.e. the vector is located within a tissue, an organ or an animal at a distance from the localisation and/or in a distance from the point in time of administration of the inductor.

OBJECTS OF THE INVENTION

The present invention seeks to overcome shortcomings of the known state of art in respect of bacterial vectors, especially their disadvantage of being essentially uncontrolled.

In a first embodiment, it is an object of the present invention to provide a system of pharmaceuticals for medical use as live vaccines. In this respect, the present invention especially seeks to provide a system of pharmaceuticals, which are applicable systemically, nasally, orally, rectally and/or otherwise mucosally and which can be used to elicit a systemic immune response and/or one that is present within the mucosa associated lymphoid tissue of the intestiny and/or mucosa of the respiratory organs and/or of the genitals.

For the development of potent vaccines, especially against infections transmitted via mucosal tissue, like infectious microorganisms, parasites, and viral infections like HIV, it is desirable for the vaccine to elicit cellular immune responses and/or antibody responses. The design of the bacterial vector, e.g. choice of the appropriate bacterial strain, allows to induce immune responses in the mucosa and/or systemically. Accordingly, the present invention also seeks to provide bacterial vectors for vaccines eliciting a humoral and/or cellular immune response both within mucosa and systemically based on non-invasive as well as on invasive bacteria, preferably attenuated strains.

In order to control the activity of genetically manipulated attenuated invasive bacteria during their presence adjacent target cells and/or during their infection of target cells, which may be cultivated cells, cultivated or extracorporal tissue or extracorporal organs, preferably specific tissue or organs within an animal, the present invention seeks to provide a regulatory component acting in combination with the vector component to provide control by exertion of an influence external to the bacterial vector as well as external to the target cell and at will to regulate the activity of functionally linked nucleic acid sequences, e.g. of a transgene forming part of an expression cassette.

In a second embodiment, it is an object of the present invention to provide a combination of pharmaceutical preparations for medical use for the delivery of peptide and/or nucleic acid sequences for immunization, gene therapy, or other biologically active compounds, e.g. probiotic or functional food applications, e.g. for the delivery of beneficial factors within the intestiny of an animal, hormones, antibody, immunomodulating substances, or pro-drug converting enzymes.

In a third and fourth embodiment, it is an object of the present invention to provide a combination of pharmaceuticals for medical use in tumor therapy and for diagnostic purposes, respectively.

In a fifth embodiment, it is an object of the present invention to provide a combination of compounds acting as an insecticide or vermicide realizing a tight control system which allows the arbitrary activation of the insecticidal and vermicidal activity, respectively.

Apart from the need for the regulatory system to be responsive to an external inductor or repressor substance, a very tight control of the activity is preferred. Tight regulation by a regulatory element has the desired effect to substantially eliminate any activity of the transgene sequences functionally linked downstream in order to substantially avoid the presence of ribonucleic acid sequences and/or peptide and/or minimize the presence of plasmid DNA within the bacterial vector which can be detrimental to the vector's infectivity or detrimental to its transfer rate of the functionally linked gene product and/or nucleic acid sequence into the mammalian cell.

In this respect, it has been found in preliminary experiments that expression of a heterologous peptide within a bacterial vector, for example under control of a constitutive promoter sequence, decreases its infectivity. Furthermore, high copy number plasmids encoding the desired peptide for transfection into a mammalian cell, although in principle preferable due to the higher content of the desired sequences, also result in a decreased infectivity of the bacterial vector in addition to being unstable within the vector in the absence of a selective pressure.

GENERAL DESCRIPTION OF THE INVENTION

The present invention achieves the above-mentioned objects by making use of the surprising finding that induction of RNA transcription and/or translation of protein from the transgene under the control of a saccharide inducible promoter within bacterial vectors can be induced even when the bacterial vector is present in an animal like a mammalian organism, e.g. when the bacterial vector has been introduced to the animal or human being by concurrent or later introduction of the inductor saccharide to the animal or human being.

For achieving the above-mentioned objects, the present invention provides the use of a bacterial vector, genetically manipulated to contain at least one transgene under the control of a saccharide inducible promoter, for administration to an animal for medical purposes, including the use as a functional food and/or for probiotic food applications, in combination with the use of the inductor saccharide for administration to an animal for medical purposes in order to induce the saccharide inducible promoter by separate administration to the animal. Preferably, the administration of inductor saccharide is carried out concurrent or subsequent to the administration of the bacterial vector.

Accordingly, the present invention can make use of the property of bacterial vectors to preferentially migrate to and replicate in specific body regions, tissues or organs, e.g. professional antigen presenting cells or tumor tissue. By administration of the inductor saccharide to the animal or human simultaneously with the introduction of the bacterial vector, but preferably some time past the introduction of the bacterial vector, and without the necessity to apply the inductor saccharide within the vicinity of the bacterial vector, induction of the saccharide inducible promoter is arbitrarily controllable.

In relation to the invention, reference to arbitrary activation of the saccharide inducible promoter, i.e. transgene activation, refers to the property of the invention to provide control of transgene activation essentially independent from the environment of the bacterial vector at the desired site of transgene activation, e.g. controllability by application of an inductor substance by an arbitrary act.

It has been found surprisingly that the administration of the inductor saccharide to an animal that has concurrently or previously received a bacterial vector containing a transgene under the control of a saccharide inducible promoter is a feasible way to control activity, i.e. transcription and/or translation of the transgene, essentially independent from the localization of the bacterial vector within the animal.

In addition to overcoming the previously accepted necessity to directly apply the inductor saccharide within the immediate vicinity to a bacterium containing a transgene under the control of a saccharide inducible promoter, the present inventors have found that administration of the inductor saccharide in a distinct manner, and separately from the bacterial vector, i.e. without a close co-localization within a limited space to the bacterial vector, can still be used to induce the saccharide inducible promoter within the bacterial vector. Accordingly, oral, mucosal or systemic administration of the inductor saccharide to an animal that concurrently or previously has received bacterial vectors, independently by oral, mucosal or systemic administration, can be used to deliver nucleic acid and/or protein from the bacterial vector to cells, tissue or organs, e.g. tumor tissue, within the animal.

Further, it has been found that the present invention advantageously allows to induce transcription and/or translation of the transgene under the control of a saccharide inducible promoter in a concentration dependent manner, i.e. by varying the amount of inductor saccharide that is administered to the animal that has received the bacterial vector.

Accordingly, the present invention uses a bacterial vector and an inductor saccharide suitable for inducing an activity from the bacterial vector for producing a system or a combination of pharmaceutical preparations, comprising as a first compound a bacterial vector for administration for medical purposes, genetically manipulated to contain a transgene under the control of a saccharide inducible promoter and, as a second component, the inductor saccharide for administration for medical purposes for induction of the saccharide inducible promoter while the bacterial vector is present within an animal, e.g. within a mammal or a human patient to be treated.

Generally, the pharmaceutical combination according to the invention is used for transcribing and/or translating the transgene contained in the bacterial vector concurrent to or, preferably, after its administration to an animal by the use of the inductor saccharide for administration to the animal for inducing the saccharide inducible promoter. In the present invention, the use of bacterial vectors for medical purposes is comprised in the combination with the use of the inductor saccharide as a pharmaceutical compound for induction of the saccharide inducible promoter in a controlled manner, preferably by administration of the bacterial vector separate from the administration of the inductor saccharide. Bacterial vectors can be administered systemically, nasally, orally, rectally and/or otherwise mucosally in combination with the concurrent or subsequent administration of the inductor saccharide, essentially without limitations to the route or point in time of the administration in relation to the administration of the bacterial vector, in order to transcribe the transgene functionally linked to the saccharide inducible promoter.

In a preferred embodiment, the combination of compounds according to the present invention is used firstly for the administration of the bacterial vector and, at a second, later point of time, for the administration of the inductor saccharide to the same animal. In this embodiment, the properties of the bacterial vector to migrate to and/or replicate in certain tissues or organs within the mammalian body is utilized to deliver nucleic acids and/or protein to the region, where the bacterial vector accumulates. Surprisingly, it has been found that induction of the saccharide inducible promoter is possible by administration of the inductor saccharide to the animal, e.g. orally or systemically, is effective and essentially independent from the localization, that the bacterial vector has reached.

In the embodiments of the invention, a pharmaceutical system or combination comprising two compounds for concurrent, preferably for subsequent administration is provided, namely a first component comprising a bacterial vector which is genetically manipulated to contain a transgene functionally linked to a saccharide inducible promoter and, as a second component, comprising the inductor saccharide. Accordingly, the present invention provides the use of a bacterial vector for production of a first component of a pharmaceutical system of compositions and the use of the inductor saccharide for production of a second component of the pharmaceutical system of compositions. In this pharmaceutical system or combination of compositions, the first component serves to introduce the nucleic acid sequences encoding the transgene under the control of the saccharide inducible promoter into the animal according to the route of administration and, predominantly, according to migration and accumulation of the vector within the animal; the second component serves for activation, e.g. induction of the first component by its administration to the animal that contains, e.g. by concurrent, preferably by previous administration, the first component.

Controlled induction of the transgene activity by the second component allows to regulate transcription of the transgene at the desired localization and time. A bacterial vector used as the first component for vaccination can introduce a transgene encoding an antigenic peptide into target cells and/or by using a very low copy number plasmid encoding the antigenic peptide, also bearing a high copy number origin of replication under the control of the saccharide inducible promoter.

In a first embodiment, the pharmaceutical combination according to the invention can be used to elicit a systemic immune response and/or one that is present within the mucosa associated lymphoid tissue of the intestiny and/or mucosa of the respiratory organs or of the genitals.

In a second embodiment, the pharmaceutical combination according to the invention can be used for the delivery of pharmaceutically active compounds to specified tissue regions within an animal, e.g. nucleic acid sequences, e.g. for gene therapy, or hormones, immuno-modulating substances, reactive RNA species or other biologically active compounds, e.g. immuno-reactive peptides for immunization, antibody, apoptose-inducing factors, or pro-drug converting enzymes.

The combination of a bacterial vector component with the inductor component can advantageously be used for producing pharmaceutical preparations for use in tumor therapy, by itself or in combination with known pharmaceuticals or methods for tumor treatment, e.g. in combination with chemotherapy and/or with irradiation. For use in tumor therapy, several bacterial species are suitable for generation of the bacterial vector component, e.g. non-pathogenic obligate anaerobic or facultative anaerobic bacteria which invade and selectively replicate within tumor, preferably solid tumors. However, attenuated strains of originally pathogenic bacteria can also be used for generating the bacterial vector component. The bacterial vector component of the invention in this embodiment is efficient to deliver peptide and/or nucleic acid sequences to tumor tissue upon application of the inductor saccharide because the properties of the vector to preferentially, preferably selectively, colonize tumor tissue are realized during this use of the bacterial vector component for medical purposes.

Accordingly, in a third embodiment, the pharmaceutical combination according to the invention is used for the treatment of tumors like cancer or other neoplastic tissue. In this embodiment, the natural preference of some bacteria that are used as bacterial vectors according to the invention for accumulation in and/or around tumor tissue is utilized, e.g. of *Salmonella*, *E. coli* and *Clostridium*, even to colonize tumor tissue. Preferably, subsequent to the localization of bacterial vector in the vicinity of tumor tissue, e.g. the colonization of a tumor, administration of the inductor saccharide by a route independent from the localization of the bacterial vector and at a later point in time, e.g. after colonization of tumor tissue by bacterial vector, is used.

According to the fourth embodiment of the present invention for use in diagnostics and/or treatment of tumors, e.g. cancer, the bacterial vector component is provided with a monitoring transgene, characterized by encoding a product which can be monitored by detection of its activity using spectroscopical analysis. As monitoring transgenes, genes for luminescent and/or fluorescent proteins, e.g. GFP, eGFP, lux gene products, e.g. obtainable from *Photorhabdus luminescens*, luciferase as well as enzymes converting a pro-compound to a compound resulting in an increased signal in analytical expression can be used. As a result, presence and localization of bacterial vector can be followed, e.g. for identification of localization of tumor tissue and metastatic carcinoma, and for an assessment of localization and of the number of bacterial vector distributing in and colonizing the tissue, organ or animal, optionally also over the course of administration of inductor saccharide.

In this embodiment, the bacterial vector may in addition to the monitoring transgene contain a transgene that provides anti-tumor activity, e.g. cytokines, antibody or toxic products, wherein the transgene is under the control of a saccharide inducible promoter, which is a different or the same as the saccharide inducible promoter controlling the monitoring transgene.

For the purpose of this disclosure, the term "animal" refers to vertebrates, e.g. to fish and to mammals, e.g. to farm and pet animals like dogs, cats, sheep, cattle, horses, camels, goats, preferably to humans, as well as to wild animals like vermin and insects.

In relation to vermin and insects, which are regarded as pests, the combination according to the invention can be used as an insecticide and vermicide, respectively. In this fifth embodiment, the transgene to be induced within the animal after uptake of the bacterial vector by administration of the inductor saccharide is chosen to act as a poison, preferably specific poison to the vermin and insects, respectively.

For constructing bacterial vectors, non-invasive or invasive bacteria can be used, genetically manipulated to comprise a saccharide inducible promoter controlling a nucleic acid sequence encoding the transgene. Induction of the saccharide inducible promoter causes transcription of the transgene, producing an RNA, e.g. an inhibitory RNA (iRNA), small interfering RNA (siRNA), or an mRNA, translatable into protein. As induction of the transcription of the transgene according to the invention within an animal or a human being is essentially independent from the localization which the bacterial vector has reached within the animal, transcription occurs at the site of accumulation of the bacterial vector, transcription and/or translation of the transgene occurs at the site of localization of the bacterial vector, i.e. extracellularly and/or intracellularly within the animal tissue. Depending on the transgene, the bacterial vector serves as a transport vehicle for the nucleic acid encoded by the transgene and/or for peptide translated from the transgene. Release of nucleic acid and/or peptide synthesized by the vector can also be obtained by partial or complete lysis of the bacterial vector, controlled by a saccharide inducible promoter and/or by secretion of peptide translated from the transgene.

The bacterial vectors for use in the pharmaceutical combination according to the invention are based on non-invasive, e.g. commensal bacteria or on invasive bacteria, which are preferably attenuated, and which are useful for introducing peptide and/or nucleic acids into or adjacent to target cells or organisms. These bacterial vectors comprise a transgene, for example containing an expression cassette for a peptide and/or an expression cassette regulating an origin of replication and/or an expression cassette encoding untranslated RNA, wherein the expression cassette is operably linked to and under the control of a saccharide inducible promoter as the specific regulatory element. As a further embodiment, the transgene may in addition to nucleic acid sequences functionally linked to the saccharide inducible promoter comprise protein encoding nucleic acid sequences, which are linked in one operon encoding two or more proteins, e.g. synthetic pathway enzymes. Further, different transgenes may be comprised in the bacterial vector, functionally linked to different saccharide inducible promoters to allow for separate induction of transgene activity by administration of the respective inductor saccharide.

The transgene is operably linked to the saccharide inducible promoter, forming an expression cassette within the genome of the bacterial vector or, alternatively, on one plasmid replicable or maintainable within said bacterial vector. The transgene may be present within an expression cassette under the control of the saccharide inducible promoter, or its expression may be controlled indirectly by regulating the copy number of the transgene under the control of the saccharide inducible promoter. In the latter case, the saccharide inducible promoter indirectly controls the activity of the transgene by directly controlling the activation factor (e.g. a replicase) acting on an inducible origin of replication linked to the transgene.

According to the invention, the saccharide inducible promoter originates from operator regions of bacterial origin, which are regulatable by saccharides, for instance inducible by increasing concentrations of a saccharide. In its preferred form, the inventive saccharide inducible promoter is gradually inducible, responding gradually to increasing concentrations of the saccharide.

Examples for the saccharide inducible promoters to be used according to the invention are regulatory regions controlling catabolic enzymes of the bacterial degradation pathway of saccharides, for example the promoters encoding catabolic enzymes of the rhamnose or xylulose pathway, and, most preferably the arabinose promoter element $P_{BAD}$ from *E. coli* or a promoter from the ara-operon of *Bacillus subtilis*. The inductor substance for the saccharide inducible promoters to be used in connection with the invention are the corresponding saccharides, i.e. rhamnose in the case of the promoter element from the rhamnose operon, xylulose in the case of the promoter element from the xylulose operon, and L-arabinose in the case of the arabinose promoter. Activation of the saccharide inducible promoter is obtained by adding the respective saccharide inductor to the culture medium of cells, tissue, organs or to an organism, respectively.

The preferred saccharide inducible promoter to be used within the bacterial vectors according to the present invention is the promoter $P_{BAD}$ of the L-arabinose operon of *E. coli* regulating the transcription of the gene product araB (ribulokinase), araA (isomerase) as well as araD (epimerase). This promoter is regulated by the gene product araC, whose transcription is repressed by AraC itself. In the absence of L-arabinose, AraC forms a homodimer, binding to the initiator region 1 (I1) and the operator region 2 (O2), forming a DNA loop upstream of the $P_{BAD}$ resembling a termination loop which represses $P_{BAD}$. When L-arabinose is present, AraC accepts L-arabinose into its binding pocket, changes its conformation and releases the DNA loop formation. Further, AraC as a homodimer with L-arabinose bound then binds to the initiator regions 1 and 2 (I1, I2) upstream of $P_{BAD}$, allowing both binding of the activating complex formed by cyclic AMP (cAMP) and cAMP receptor protein upstream of the regions I1 and I2 as well as allowing the binding of RNA polymerase downstream from the regions I1 and I2, thus effectively starting transcription from the promoter element $P_{BAD}$. For a detailed description of the L-arabinose operon in *E. coli*, see Schleif, *BioEssays* 25.3, pp. 274-282 (2003).

As an alternative to using saccharides which are metabolizable by the bacterial vector and/or by the recipient animal for induction of the saccharide inducible promoter, analogons and derivatives of the saccharide can be used as inductor saccharides. Analogons and derivatives of the saccharides are e.g. sugar alcohols, sugar isomers, as well as esterification, amidation, alkylation or alkoxylation products of sugar, which are included in the term inductor saccharide for the purposes of the invention.

One of the considerable advantages of the saccharide inducible promoters to be used according to the present invention, especially of the preferred promoter element $P_{BAD}$, is their tight regulation in the absence of inductor. Therefore, also structural genes encoding peptides which are potentially toxic to the bacterial vector, for instance the gene E of bacteriophage Φ X174, may be functionally linked to $P_{BAD}$ and be present within the bacterial vector according to the invention. Similarly, tight control of expression of a replicase acting on an inducible origin of plasmid replication is required. The tight regulation of the promoter activity allows to create bacterial vectors containing DNA sequences, the activation of which would be detrimental to the viability or to the infectivity of the bacterial vector or would result in the loss of the plasmid containing these sequences.

A further advantage of the promoter element $P_{BAD}$ is its response to gradually increasing concentrations of the inductor substance L-arabinose in the form of gradually increasing activity.

The inductor saccharides used as inductors for the saccharide inducible promoters have the advantage of being non-toxic to the host cells and organisms targeted by the bacterial vector, e.g. to animals, and non-toxic to other cells of a target organism. Furthermore, saccharides can be administered by one of several routes (e.g. orally or systemically, i.e. intravenously, peritoneally, parenterally or intramuscularly) to spread through an animal or human organism to reach the bacterial vector according to the invention. Therefore, induction of the saccharide inducible promoter contained in the bacterial vector to transcribe the functionally linked expression cassette, e.g. to activate the pre-determined activity encoded by the vector, is feasible in a very simple manner. Especially the preferred inductor substance L-arabinose is in wide use for dietary purposes as well as a formulation agent for pharmaceutical preparations and, accordingly, its harmlessness in view of mammalian cells, for example cultured cells, tissue, organs or mammalian organisms is proven.

Furthermore, a saccharide to be used as an inductor substance offers the advantages of being readily available at low cost and of administration by established routes, for example orally or intravenously.

In a first aspect, the present invention provides a pharmaceutical combination for controlled peptide delivery into an animal organism, e.g. into the vicinity of target cells in vivo. For this use, vectors that form the first component of the pharmaceutical system are based on non-invasive bacteria or on invasive bacteria. Synthesis of an antigenic peptide encoded by said bacterial vector is induced by application of the inductor saccharide, e.g. the pharmaceutical combination of the invention resulting in the effect of a live vaccine for animals including humans. The use as vaccines can be directed to preferentially induce a cellular and/or humoral immune response, by appropriate choice of the bacterium used for the vector and on the peptide encoded by the transgene.

It is a specific advantage of the present invention that the bacterial vector component of the pharmaceutical combination according to the invention can be chosen to preferentially induce a cellular and/or humoral immune response, depending on the properties of the bacterium used and/or on the properties of the peptide encoded by the transgene. In detail, it has been found that both non-invasive bacteria and invasive bacteria lead to or can be adapted to preferentially direct the immune response to a cellular or a humoral one. However, a person skilled in the art can easily determine which bacterium constitutes a suitable component for a bacterial vector in combination with the peptide encoded by the transgene in the pharmaceutical system to achieve the desired cellular and/or humoral immune response.

An example for an analytical method to determine the induction of humoral immune responses in serum of recipient animals is an ELISA for antigen-specific antibodies. An example for an analytical method to determine the induction of cellular immune responses in different locations of recipient animals is the analysis of cytokine production by antigen-specific immune cells.

Here, bacterial vectors that are based on non-invasive bacteria like e.g. commensal bacteria, are used for the delivery of peptide encoded under the control of the saccharide inducible promoter. Bacteria commensal to animals or humans can be used to express and/or release peptide or synthetic pathway enzymes to produce effector molecules. Effector molecules can be provided by the pharmaceutical combination of the invention using bacterial vectors expressing synthetic pathway enzymes for e.g. interleukins, leukotrienes as well as drugs obtainable from pro-drugs by enzymatic conversion.

An exemplary enzyme for the conversion of a pro-drug to a more potent drug is cytosine deaminase, e.g. from E. coli.

Not only are these activities of the vector induced at will by applying the inductor saccharide to the animal or human having received said vector, but further, repeated activation of the transgene is possible by application of the inductor saccharide, as long as bacterial vector is present.

For introducing peptide into the cells of animals treated with the pharmaceutical combination of the invention, its vector component is preferably based on attenuated invasive bacteria. Target cells are tissue or organs within an animal, i.e. in vivo, cultivated animal cells or extracorporal tissue or organs. Herein, attenuated invasive bacteria serve as a transport vehicle for introducing transgene sequences into animal cells, which transgene sequences are transcribed and/or translated by the bacterial component. Dependent on the nature of the peptide encoded by the vector, the vector is for medical use or for technical use, e.g. for manipulating cultivated target cells, e.g. for the extracorporal treatment of organs.

Additionally or in the alternative, the bacterium on which the bacterial vector component is based serves to enhance the specific immune response desired against the peptide expressed, e.g. the bacterium acts as an adjuvant for antigenic peptides. In accordance with the antigenic properties of the peptide encoded by the transgene and depending on the cellular and humoral components of the immune response elicited, such a bacterial vector can constitute the first component of the pharmaceutical combination used as a vaccine against viral or bacterial infection or against parasites, tumor cells, or factors involved in autoimmunity or allergy, against Alzheimer plaques and other malignancies.

Alternatively, the transgene may encode a suicide gene whose synthesis leads to lysis of the bacterial vector and subsequent release of its constituents, predominantly into the vicinity of target cells in the case of vectors based on non-invasive bacteria, and predominantly within target cells in the case of vectors based on attenuated invasive bacteria, respectively.

In a further aspect, the bacterial vector component is based on non-invasive or on attenuated invasive bacteria for delivery of nucleic acids, which can be transcribed and/or translated by the recipient mammalian cell. This can be used for introducing a desired nucleic acid sequence into the vicinity of or into target cells within an animal or within an extracorporal organ. In one aspect, the vector component is used as a transport vehicle for introducing exogenous nucleic acid sequences into animal organisms or cells, for example DNA comprising an expression cassette encoding a peptide homologous to the recipient mammalian cell or encoding a heterologous peptide, for example having antigenic properties to elicit an immune response from the recipient organism. The transfer of an expression cassette encoding an immunogenic peptide instead of the direct transfer of the antigen is also termed DNA vaccination.

For use in vaccination, the pharmaceutical combination according to the invention allows the advantageous delivery of a transgene because the transgene can be maintained within the vector component until delivery of peptide and/or nucleic acid to the vicinity of or into the target cell essentially without activity of the transgene previous to the administration of its second component. The advantage of induction of transgene activity by administration of the inductor saccharide becomes evident when looking at the energetic burden to the bacterial vector for maintenance of a transgene within a plasmid or for continued peptide synthesis during the course of infection, reducing the efficiency of the vector component. As target cells reached by the vector component, Peyer plaques and further immunoreactive tissues of animals have been identified to contain bacterial vector after oral and systemic administration of the vector, respectively. Activation of the transgene could be achieved in these immunoreactive target cells by subsequent oral or systemic administration of the inductor saccharide.

A further medical use of the pharmaceutical combination, which preferably contains a bacterial vector component, using a vector generated on the basis of non-invasive or invasive bacteria, which in the case of pathogenic bacteria are preferably attenuated, is marking, identification and/or killing of tumor cells. Here, the transgene may be a peptide which is recognized by the recipient animal as an antigen when available for presentation in complex with MHC molecules. The antigen may be heterologous peptide or a self-antigen to break self-tolerance. Marking or identification of tumor cells for subsequent elimination by CTL is an efficient way of surmounting the self-tolerance which is an obstacle to the attack of CTL against tumor cells. The complex of antigen delivered by the bacterial vector component and MHC I is then recognisable by cytotoxic T-lymphocytes. This leads to the generation of cytotoxic T-lymphocytes, directed against cells presenting the immunogenic peptide on their superficial MHC I complex. When used in connection with the preference of some enteropathogenic bacteria, for example salmonella or E. coli, to invade tumor tissue and replicate therein, the bacterial vector component of the pharmaceutical system directs the cellular immune response involving cytotoxic T-lymphocytes against identified cells, preferably against tumor tissue.

For use in tumor therapy, the transgene contained within the bacterial vector component can be selected from nucleic acids encoding factors that suppress the expression and/or activity of oncogenes, e.g. iRNA, pro-drug converting enzymes, e.g. E. coli deaminase, cytotoxic proteins, e.g. colicin E3, immunomodulating factors, e.g. cytokines, the tumor necrosis factor alpha (TNFalpha), and/or anti-angiogenic factors, e.g. endostatin.

Synchronizing the time of administration of the inductor component with the infectious cycle or migration of the bacterial vector component within the target organism that has been administered the vector component to specific or non-specific tissues, cells and/or cellular compartments, e.g. after completion of migration into tumor tissue is expected or determined, allows to start the desired activity from the saccharide inducible promoter at desired locations.

This desired activity may be the synthesis of an antigen intended for presentation on the surfaces of specific target cells, i.e. on the outside of tumor cells to mark them for recognition by T-cells. Another example for the desired activity is the synthesis of an apoptose-inducing factor, or of a peptide catalyzing the conversion of a pro-drug to a drug, resulting for example in an increased cytotoxicity of the drug compared to the pro-drug. A further desired transgene activity may be the synthesis of bacterial toxins, e.g. cytotoxins. These bacterial vector components preferentially comprise a transgene encoding a peptide, the expression of which within the infected tumor cell induces apoptosis or lysis by cytotoxic T-cells. For diagnostic or research purposes, tumor tissue can be identified by introduction of an expression cassette containing a product that can be identified spectrometrically, for example a fluorescent or bioluminescent peptide or peptide catalyzing the conversion of a compound to generate a detectable signal, e.g. a magnetosome or luminescence.

As a further embodiment of the invention, the bacterial vector component is genetically manipulated for enhanced expression of the inductor saccharide transporter system importing the inductor saccharide into the vector. This genetic manipulation can be effected by enhancement of the basal promoter activity controlling expression of the inductor saccharide transporter system or, alternatively, by introduction of the expression cassette encoding the inductor saccharide transporter system, e.g. into bacteria used as vectors that originally are devoid of an inductor saccharide transporter system for the inductor saccharide suitable for inducing activity of the saccharide inducible promoter controlling activity of the transgene. For example, the expression cassette encoding the L-arabinose transporter of E. coli is used to transform a bacterium lacking an L-arabinose transporter.

As a result, increased uptake of the inductor saccharide by bacterial vectors is observed, leading to enhanced induction of transgene activity. Further, the percentage of bacterial vector present that is induced is increased, reducing the effect of the so-called all-or-nothing effect that is observed at inductor saccharide concentrations in tissue below a saturating level, e.g. at medium range concentrations, leading to a considerable proportion of bacterial vector without inductor saccharide, i.e. essentially without transgene activity. As an example, chromosomal or plasmid-based integration of a mutant lacY gene into a bacterial vector that is deficient for L-arabinose transport and/or degradation (e.g. according to Morgan-Kiss et al., PNAS 99, 7373-7377 (2002)) can be used as a genetic manipulation to enhance L-arabinose uptake and, hence, induction of the saccharide inducible promoter, in this example $P_{BAD}$.

In addition or in the alternative to the embodiment of using a genetically manipulated bacterial vector having increased activity of the inductor saccharide transporter, the bacterial vector is genetically manipulated for reduction of the metabolic pathway activity of inductor saccharide degradation. In these embodiments, genetic manipulation of the bacteria used as the bacterial vector component leads to reduction or inactivation of transcription and/or translation and/or activity of metabolic enzymes. For example, synthesis of metabolic enzymes of the L-arabinose degradation pathway (ara operon) is inactivated in the bacterial vector component.

The genetic manipulation to increase uptake of inductor saccharide and/or to reduce inductor saccharide metabolism is preferred in bacterial vectors that are not intended for repeated administration of inductor saccharide, e.g. when complete and intense induction of transgene activity is desired, e.g. lysis of the vector component when using gene E as the transgene for termination of presence of the vector.

The specificity of the bacterial vector component originates from the properties of the bacterium utilized as the first component of the pharmaceutical combination, whereas it is the second component that achieves controlled induction of the presence and, hence, activity of the transgene. Making use of the control of the vector component by administration of the inductor saccharide allows to determine, if desired repeatedly, the point of time of activation, e.g. transcription and, depending on the transgene, translation of the transgene. On the basis of identification of vector component within the animal or after lapse of a period of time the vector component needs for reaching a desired location, the spatial localisation of the vector component is utilized to achieve a spatial, i.e. a localized effect from the transgene. In this embodiment, a bacterial vector component may be used to direct the cellular immune response towards target cells displaying the antigen by MHC I, e.g. tumor cells containing the antigenic peptide originally encoded by the bacterial vector. In this regard, the bacterial component of the vector can provide adjuvant activity and serves for identification of tumor cells and localisation of the transgene activity.

The saccharide inducible promoter contained within the bacterial vector component allows for an infection of animal cells unhampered by transcription and/or translation of structural sequences and/or by a high copy number of the plasmid, due to the tight regulation exerted by this promoter in the absence of inductor saccharide. It is only after the external administration of the inductor saccharide at any desired point of time that the desired transgene activity commences, e.g. transcription starts from the promoter.

An example for the second embodiment is the use of the pharmaceutical combination against inflammatory bowel disease, comprising a vector component based on commensal bacteria containing a transgene encoding for example interleukins, leukotrienes etc., or synthetic pathway enzymes to produce effector molecules. This bacterial vector component may be introduced into the target organism by ingestion and the synthesis of effector molecules may be induced repeatedly by subsequent ingestion of the relevant inductor component.

The transgene may encode structural genes (antigenic or immunomodulating peptide, antibody or bioluminescent peptide, toxins, e.g. bacteriostatics and/or cytostatics, enzymes modifying bacterial nucleic acids, e.g. bacterial recombinases, e.g. for altering the transgene sequence), reactive RNA species (ribozyme, antisense RNA, siRNA), a replicase for the amplification of plasmids (the trfA gene product of E. coli, acting on oriV) and/or lysis determinant of a bacteriophage (lytic peptide from suicide gene, e.g. protein E of $\Phi$ X174).

Alternatively or additionally, the transgene under the control of a saccharide inducible promoter may be used to control the copy number of the bacterial plasmid on which it is contained. For example, the transgene may encode a replicase acting on a high copy number origin of replication. Presence of the inductor saccharide leads to the synthesis of the transgene, which in turn acts on its specific origin of replication, leading to the amplification of the entire plasmid sequence. Due to the tight regulation of the inventive promoter element, such a plasmid furthermore comprises a very low copy number origin of replication in order to maintain at least one copy of the plasmid within the bacterial vector in the absence of inductor. The plasmid may comprise a further nucleic acid sequence, for example an expression cassette, optionally also under the control of a saccharide inducible promoter, encoding a structural gene or a reactive RNA species.

In order to enhance the import of nucleic acid sequences into the cellular nucleus, enhancer elements for nuclear import can be present on such nucleic acid sequences, for example the cPPT region, (poly purine tract, a genetic element enhancing nuclear import).

Further transgenes which can be encoded by bacterial vector components may additionally or alternatively encode a suicide gene under the control of the saccharide inducible promoter. Such a suicide gene catalyzes the lysis of the bacterial vector component and may be represented for example by the lysis gene of phage $\Phi$X174, gene E. The presence of a transgene encoding a suicide gene is only possible under the control of a tightly regulated promoter as the lysis of the bacterial vector is induced by the synthesis of only a few molecules, for example of less the 100 molecules of gene E product. Therefore, presence of the inductor saccharide leading to the synthesis of the suicide gene product results in the rapid destruction of the bacterial vector component and in the release of its contents into the phagosome, the cellular cytosol and/or into the intercellular space. Accordingly, a suicide gene under control of a saccharide inducible promoter can be used for genetically manipulated bacterial vector components as a safety feature for aborting their presence and for the release of the bacterial content.

In order to destroy the phagosome in the case of intracellular bacteria replicating therein, the bacterial vector component may be genetically manipulated to comprise a transgene for secretion of a peptide leading to the destruction of the phagosome, for example listeriolysin O (LLO). The peptide leading to the destruction of the phagosome may be activated by administration of the inductor component. This phagosomal lysis facilitates the liberation of the bacterial vector's contents into the cytosol, which allows access of peptides for presentation via MHC-I and/or the nuclear import of nucleic acid sequences into the cellular nucleus.

A further example for a structural gene to be used as the transgene are sequences encoding peptides useful for research, monitoring and diagnostic purposes, for example green fluorescent protein and its homologues or derivatives, luciferase or the lux operon (lux CDABE) of *Photorhabdus luminescens* for detection of luminescence, for example by a CCD camera, or via enzymatic activity generating a dye, e.g. beta-galactosidase.

Further examples of transgenes are secretory proteins, conjugational DNA-protein complexes, bacteriolytic determinants or bacteriophage for release of macromolecules from the vector within the tissue, organ or animal upon induction by administration of inductor saccharide. Secretion systems usable for secretion of transcription and/or translation products of the transgene or of DNA, respectively, are for example bacterial secretion systems and, alternatively, bacteriophages and lysis systems, modified for the transfer and/or release of macromolecules from the bacterial vector. Secretion systems comprise type I secretion systems like the *E. coli* hemolysin secretion system, which be adapted to the saccharide regulated secretion of peptide by generation of transgene encoding a fusion peptide containing the secretory recognition sequence. Similarly, the general secretion pathway (Sec) of *E. coli*, classified as type II secretion system, and type III secretion systems, e.g. *E. coli* flagella type III secretion system or pathogenicity related type III secretion systems of Salmonella can be adapted by the generation of a transgene encoding a fusion peptide with the respective signal peptide. One specific use of the type III secretion systems is the translocation of peptide from extracellular bacteria into target cells or from bacteria residing in intracellular compartments of the host cell into the cytosol. Further, type IV secretion systems, also referred to as conjugational apparatuses, e.g. the VirB/VirD4 type IV secretion system of *Agrobacterium tumefaciens*, can be adapted for secretion and/or translocation of peptide and/or DNA by providing the transgene with a nucleic acid sequence encoding the respective signal sequence specific to the secretion system. One specific use of type IV secretion systems is the translocation of peptide and/or DNA from extracellular bacteria into target cells or from intracellular bacteria across cellular compartmental borders, according to the invention within the animal after induction by administration of the inductor saccharide. Alternatively or additionally, autotransporter and other surface-display systems, e.g. the *E. coli* AIDA autotransporter, can be used as transgene. Bacteriophages, e.g. phages Lambda or M13, can be used as a transgene, effecting their release from the bacterial cell upon induction by the inductor saccharide. Whereas the release of Lambda phage requires bacterial cell lysis, the filamentous phage M13 can be secreted by the viable bacterial cell. Lysis determinants, e.g. protein E of bacteriophage phiX174 or protein Hok of plasmid R1, can be used as transgenes for lysis of the bacterial vector giving rise to the release of peptide and/or nucleic acid from the bacterial vector.

In one embodiment of the present invention, the bacterial vector component is genetically manipulated to enhance the activity of its intrinsic secretory system to increase secretion of a transcription or translation product of the transgene upon administration of the inductor saccharide. Alternatively, the bacterial vector component is genetically manipulated to comprise a chromosomal or plasmid-based expression cassette encoding a secretory system for the enhancement of secretion of the transcription or translation product of the transgene. For these purposes, the above mentioned secretion systems type I to IV can be used.

Bacteria that can form the basis for the vector component of the pharmaceutical combination according to the invention comprise artificial bacteria carrying substantial deletions in comparison to wild-type strains and/or comprising genetic determinants of several different bacteria as long as they still provide for the function of the bacterial vector component in the combination according to the present invention, and attenuated strains of non-pathogenic or pathogenic gram-positive and gram-negative bacteria which may be invasive or non-invasive to animal cells, or commensal bacteria. The gram-negative bacteria are for example *E. coli, Salmonella* spp., e.g. *Salmonella enterica* serovar *Typhimurium*, like strain SL7207, e.g. *Salmonella enterica* serovar Typhi, like strain Ty21a, *Shigella* spp., *Yersinia* spp., and *Vibrio cholerae*. Examples for gram-positive bacteria are *Bacillus* spp., e.g. *Bacillus subtilis, Clostridium* spp., *Listerium monocytogenes*, and *Mycobacterium* spp., e.g. strain BCG. Commensal bacteria are for example *E. coli, Lactobacillus* spp., *Lactococcus* spp., and *Streptococcus gordonii*.

Within the terms of this disclosure, the expression "attenuated invasive bacteria" especially refers to attenuated strains of *E. coli, Listerium monocytogenes, Salmonella enterica* var. *typhimurium, Shigella flexneri, Yersinia pseudotuberculosis*, and attenuated strains of further invasive bacteria as well as of the non-invasive bacterium *Vibrio cholerae*. The reason for including *Vibrio cholerae* for the purposes of this disclosure within the term "invasive bacteria" is that for *Vibrio cholerae* attenuated strains exist, which have been demonstrated to accumulate within tumor tissue (Nature Biotechnology, Volume 22, No 3, March 2004). With reference to the affinity of *Vibrio cholerae* to tumors this is a property shared with at least some invasive bacteria, making them useful within the present invention.

In the context of this disclosure, the classification of bacteria useful as the bacterial vector components of the invention as invasive or non-invasive includes the possibility for some bacteria to colonize organ specific tissue intracellularly and extracellularly. This applies for example to Salmonella, that colonize tumor tissue also in an extracellular state.

Further, invasive bacteria can be used to generate the vector component of the invention which originally are non-invasive bacteria but which have been rendered invasive by genetic manipulation, e.g. by introduction of coding sequences for invasion promoting factors, e.g. the invasin gene (inv) derived from *Yersinia pseudotuberculosis*, e.g. by expression in *E. coli*.

Further exemplary bacteria suitable for producing the bacterial vector component of the pharmaceutical combination according to the invention are: *Agrobacterium* e.g. *Agrobacterium tumefaciens; Bacillus* e.g. *Bacillus cereus, Bacillus subtilis, Bacillus thuringiensis, Bacillus weihenstephanensis; Bartonella* e.g. *Bartonella henselae, Bartonella schoenbuchensis; Bdellovibrio* e.g. *Bdellovibrio bacteriovorus, Bdellovibrio starri, Bdellovibrio stolpii; Bifidobacterium* e.g. *Bifidobacterium adolescentis, Bifidobacterium bifidum, Bifidobacterium lactis, Bifidobacterium longum; Bordetella* e.g.

Bordetella pertussis; Borrelia e.g. Borrelia burgdorferi; Brucella e.g. Brucella abortus, Brucella bronchiseptica; Burkholderia e.g. Burkholderia cenocepacia, Burkholderia fungorum, Burkholderia mallei, Burkholderia pseudomallei; Campylobacter e.g. Campylobacter fecalis, Campylobacter pylori, Campylobacter sputorum; Chlamydia e.g. Chlamydia pneumoniae, Chlamydiapsittaci, Chlamydia trachomatis; Clostridium e.g. Clostridium difficile, Clostridium novyi, Clostridium oncolyticum, Clostridium perfringens, Clostridium sporogenes, Clostridium tetani; Corynebacterium e.g. Corynebacterium diphtheriae, Corynebacterium glutamicum, Corynebacterium jeikeium; Edwardsiella e.g. Edwardsiella hoshinae, Edwardsiella ictaluri, Edwardsiella tarda; Enterobacter e.g. Enterobacter aerogenes, Enterobacter cloacae, Enterobacter sakazakii; Enterococcus e.g. Enterococcus avium, Enterococcus faecalis, Enterococcus faecium, Enterococcus gallinarum; Escherichia e.g. Escherichia coli; Eubacterium e.g. Eubacterium lentum, Eubacterium nodatum, Eubacterium timidum; Helicobacter e.g. Helicobacter pylori; Klebsiella e.g. Klebsiella oxytoca, Klebsiella pneumoniae; Lactobacillus e.g. Lactobacillus bulgaricus, Lactobacillus casei, Lactobacillus delbrueckii, Lactobacillus plantarum; Lactobacterium e.g. Lactobacterium fermentum; Lactococcus e.g. Lactococcus lactis, Lactococcus plantarum; Legionella e.g. Legionella pneumophila; Listeria e.g. Listeria innocua, Listeria ivanovii, Listeria monocytogenes; Microbacterium e.g. Microbacterium arborescens, Microbacterium lacticum; Mycobacterium e.g. Bacille Calmette-Guérin (BCG), Mycobacterium avium, Mycobacterium bovis, Mycobacterium paratuberculosis, Mycobacterium tuberculosis; Neisseria e.g. Neisseria gonorrhoeae, Neisseria lactamica, Neisseria meningitidis; Pasteurella e.g. Pasteurella haemolytica, Pasteurella multocida; Salmonella e.g. Salmonella bongori, Salmonella enterica ssp.; Shigella e.g. Shigella dysenteriae, Shigella flexneri, Shigella sonnei; Staphylococcus e.g. Staphylococcus aureus, Staphylococcus lactis, Staphylococcus saprophyticus; Streptococcus e.g. Streptococcus gordonii, Streptococcus lactis, Streptococcus pneumoniae, Streptococcus pyogenes, Streptococcus salivarius; Treponema e.g. Treponema denticola, Treponema pallidum; Vibrio e.g. Vibrio cholerae; Yersinia e.g. Yersinia enterocolitica, Yersinia pseudotuberculosis, including S1-strains devoid of Hfr factors and of pili of these bacteria, especially S1-strains of E. coli.

A further advantage of the promoter elements according to the invention are the absence of side effects of the inductor component, which saccharide is furthermore non-toxic, reaches cells and tissue within an animal organism, is not immunogenic, can be administered via separate routes, for example orally, intravenously or otherwise systemically, its concentration within the recipient organism or cell culture can be adjusted and it is available at low cost.

BRIEF DESCRIPTION OF THE FIGURES

The present invention will now be described by way of examples, taking reference to the accompanying figures, wherein FIG. 1 schematically depicts expression plasmid pHL238, wherein GFP is operably linked to $P_{BAD}$.

FIG. 8 schematically depicts plasmid bearing gene E of bacteriophage Φ X174 under the control of $P_{BAD}$, FIG. 9 gives the number of bacterial vector cells re-isolated from cultured macrophage cells J774A1, infected with the Salmonella enterica serovar Typhimurium strain SL7207 bearing the plasmid according to FIG. 8 after induction with various amounts of L-arabinose.

EXAMPLES

In the examples, the promoter element $P_{BAD}$ from the L-arabinose operon of *E. coli*, is present on one plasmid and/or on a DNA segment integrated at least in single copy into the bacterial vector's chromosome in combination with the structural gene for its regulator protein AraC under control of its own promoter Pc. However, the promoter element $P_{BAD}$ is only representative for saccharide inducible promoters to be used according to the invention in genetically manipulated bacterial vectors.

Figure 1:
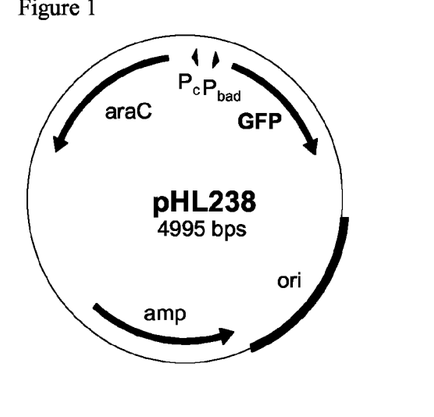

An arrangement of the saccharide inducible promoter $P_{BAD}$ with an expression cassette for its specific regulator AraC is shown in the FIG. 1, wherein the saccharide inducible promoter is arranged in a back to back relationship with the promoter Pc controlling the structural gene for its regulator AraC. This arrangement is not obligatory, however, it is essential that the expression cassette for the regulator gene is physically linked to the saccharide inducible promoter, and the arrangement of the operator elements should allow for the insertion of the desired DNA sequences downstream, i.e. in an operably linked fashion.

Example 1

Expression of Peptide from a Plasmid Contained in the Bacterial Vector after Induction As an example for a structural gene, plasmid pHL238 (schematically depicted in FIG. 1) comprising the structural gene for green fluorescent protein (GFP) under the control of $P_{BAD}$ was cloned, further comprising the structural gene for the regulator of $P_{BAD}$, araC under the control of its own promoter Pc, along with the Ampicillin resistance gene as a selection marker, and a high copy number origin of replication from pUC. Regulatory elements originate from plasmid pBAD18 (Guzman et al., *J. Bacteriol.* 1995 July; 177(14): 4121-30)

Figure 2:
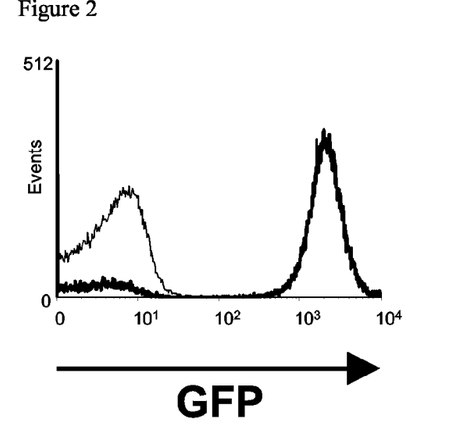
FIG. 2 shows the results of flow cytometric analysis of Salmonella enterica serovar typhimurium SL7207 bearing a plasmid according to FIG. 1 under induced and non-induced conditions, FIG. 3 the results of flow cytometric analysis of Salmonella enterica serovar typhimurium SL7207 bearing a plasmid according to FIG. 1, re-isolated from infected macrophage cells J774A1, after induction with varying concentrations of L-arabinose.

This bacterial vector is based on *Salmonella enterica* serovar *Typhimurium*, strain SL7207, which is a known attenuated invasive salmonella strain in use for experimental vaccination. The salmonella strain was transformed with plasmid pHL238 by electroporation, transformed colonies were selected on LB-medium agar plates containing streptomycin at 30 µg/mL and ampicillin at 100 µg/mL. The resultant transformed strain was bacterial vector SL7207[pHL238]. At 3 hours after addition of 0.1% w/vol L-arabinose to the bacterial culture in liquid LB medium (30 µg/mL streptomycin, 100 µg/mL ampicillin) at logarithmic growth phase, strong induction of GFP expression was monitored using a FACS-calibur flow cytometer (Becton Dickinson). Results are shown in FIG. 2, the thick line for addition of L-arabinose, the thin line without L-arabinose.

These measurements demonstrate that the synthesis of the gene product under the control of a saccharide inducible promoter by addition of the saccharide acting as its specific inductor substance leads to the bacterial expression of the structural gene. In this example, the expression of GFP leads to fluorescence values more than two orders above the background fluorescence obtained for the infected cells without induction by L-arabinose.

Example 2

Figure 3:
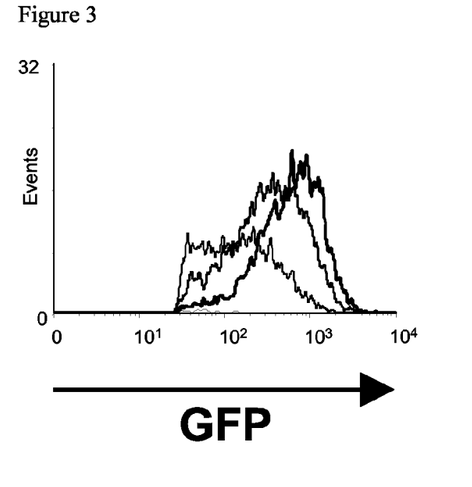

In Vitro Expression of Peptide from a Bacterial Vector after Induction within Infected Animal Cells The murine macrophage cell line J774A1 was infected with bacterial vector SL7207[pHL238] of Example 1. Before infection, cells were seeded to $2 \times 10^6$ cells per well in a 6-well plate in antibiotic-free medium (IMDM with 10% inactivated fetal calf serum, 2 mM glutamine) and grown for one day in a 5% $CO_2$ atmosphere at 37° C. For infection, SL7207 [pHL238] were grown from a glycerol stock overnight at 37° C. on a LB plate supplemented with antibiotics, followed by cultivation in liquid LB medium supplemented with antibiotics for approximately 2 hours at 37° C., shaking at 60 rpm. Bacteria were harvested by centrifugation, washed in PBS, resuspended in cell culture medium and added at a ~MOI of 10. 30 min after start of infection cells were washed twice with PBS before medium containing gentamycin (50 µg/mL) was added to kill extracellular bacteria. 4 hours after infection different amounts of L-arabinose were added into individual wells of infected J774A.1 cells up to final concentrations in of 800 µM, 4 mM, 40 mM, and 400 mM. 3 hours after addition of L-arabinose cells were treated with 0.25% Triton X-100. GFP expressing bacteria in the lysates were monitored by flow cytometry. In order to differentiate fluorescence of GFP expressing bacteria from autofluorescent cell fragments the so-called two colour flow cytometry method was used (Bumann, *Infect. Immun.* (2001) 69, 4618-4626.). The analytical results are depicted in FIG. 3, with unspecific background fluorescence substracted. Varying L-arabinose concentrations are depicted for medium without L-arabinose (thin curve) and L-arabinose at increasing concentrations at 4 mM, 40 mM and 400 mM (curves with increasing boldness).

It can be seen that the fluorescence intensity of GFP increases with increasing concentrations of L-arabinose in the medium, demonstrating the gradual induction of the saccharide inducible promoter, leading to the synthesis of GFP.

These measurements demonstrate that the introduction of a bacterial vector into mammalian cells is obtained using the bacterial vector according to the invention, and induction of the synthesis of the gene product under the control of a saccharide inducible promoter by extracellular addition of the saccharide acting as its specific inductor substance leads to the bacterial expression of the structural gene while contained in animal cells.

Example 3

In Vivo Expression of Peptide from a Bacterial Vector after Induction within a Mammalian Organism Balb/c mice were infected intravenously with a dose of ca. $5 \times 10^6$ bacteria in PBS of bacterial vector SL7207[pHL238]. After 2 days, different amounts of L-arabinose dissolved in PBS were administered intravenously into mice. 4 hours after L-arabinose administration mice were sacrificed, spleens were removed, homogenized in PBS containing 0.1% Triton X-100 and lysates were analyzed by two colour flow cytometry.

Figure 4:
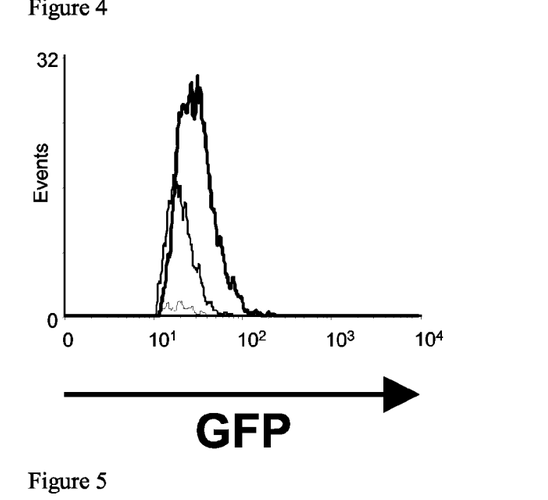
FIG. 4 shows the flow cytometric analysis of Salmonella enterica serovar Typhimurium strain SL7207 bearing the plasmid according to FIG. 1, re-isolated from the spleen of infected mice, after induction with varying amounts of L-arabinose.

It is demonstrated that expression of GFP by bacteria recovered from the infected animals was induced by L-Arabinose in a dose-dependent manner, results are depicted in FIG. 4. It is seen that the fluorescence intensity due to GFP increases with increasing concentrations of L-arabinose in the animal, demonstrating the gradual induction of the saccharide inducible promoter, leading to the synthesis of GFP.

Example 4

In Vitro Regulation of Copy Number of a Bacterial Plasmid

Figure 5:
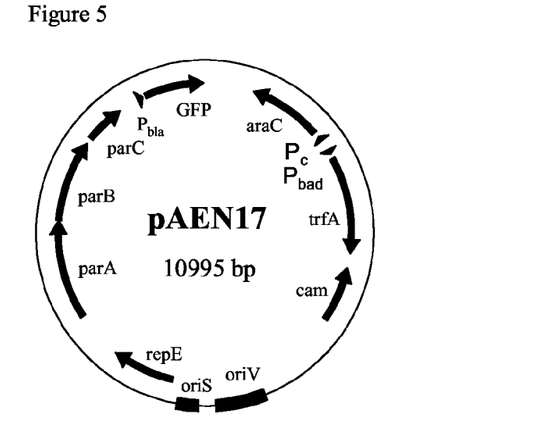
FIG. 5 depicts single copy plasmid pAEN17, containing the inducible replicon of RK2, having a constitutive expression cassette for GFP.

In order to demonstrate the regulation of the copy number of a plasmid contained within a bacterial vector, the plasmid according to FIG. 5 was constructed. In the absence of L-arabinose, just one copy of this plasmid per bacterial cell is maintained, regulated by the origin of replication derived from the F plasmid of Escherichia coli. In addition, this plasmid contains the inducible origin of replication of plasmid RK2, namely oriV. The replicase gene trfA, acting on this origin, is placed under the control of $P_{BAD}$, as an example for a saccharide inducible promoter.

Figure 6:
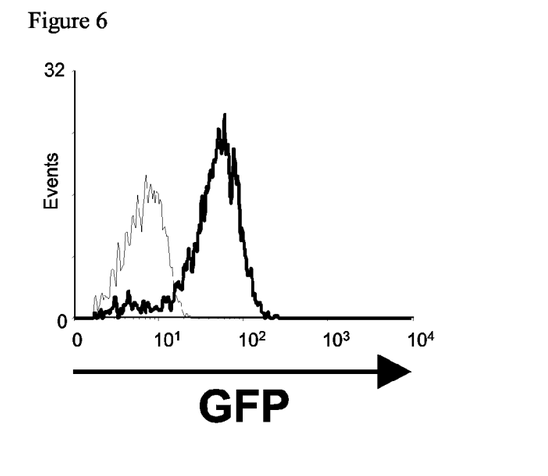
FIG. 6 shows the flow cytometric analysis of Salmonella enterica serovar Typhimurium strain SL7207 bearing a plasmid according to FIG. 5 under induced and non-induced conditions.

In order to allow for a convenient analysis of plasmid replication, GFP was placed under control of the weak constitutive $P_{bla}$ promoter derived from the bla gene, also contained on said vector. The recombinant strain SL7207 [pAEN17] was grown into logarithmic phase and either no or 0.1% L-Arabinose was added into bacterial cultures. After 3 hours of induction, plasmid replication was monitored by measuring increased GFP activity due to increased expression, which in turn was caused by plasmid amplification containing gfp gene copies, as depicted in FIG. 6.

The results demonstrate that the addition of L-arabinose induces the $P_{BAD}$, leading to the synthesis of the trfA gene product, which in turn induces replication mediated by oriV, resulting in an increased copy number of the plasmid pAEN17. The analytical results of flow cytometry are shown in FIG. 6 with background fluorescence as the left-hand peak, representing the expression of GFP at low copy number under non-induced conditions. The right-hand peak represents the activity of GFP under induced conditions, indicating the effect of the increased copy number of the plasmid and of the expression cassette for GFP, respectively. This demonstrates that a saccharide inducible promoter can be used to control the copy number of a plasmid harboured by a bacterial vector when placing the coding sequence for the gene acting on an inducible origin of replication functionally linked under the control of a saccharide inducible promoter.

Example 5

Figure 7:
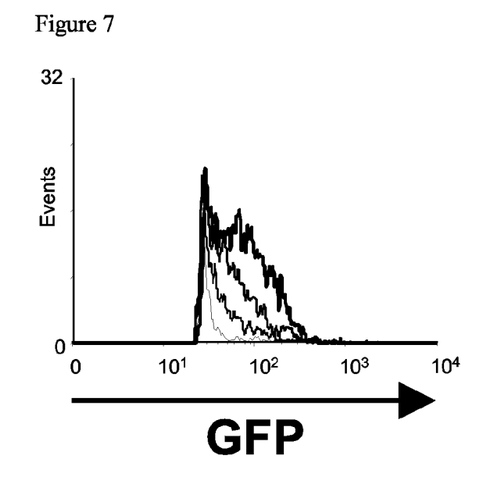
FIG. 7 shows the flow cytometric analysis of Salmonella enterica serovar Typhimurium strain SL7207 cells bearing the plasmid according to FIG. 5, re-isolated from infected macrophage cells J774A1, after induction with varying concentrations of L-arabinose.

In Vitro Induction of Plasmid Replication to Control Protein Expression from a Bacterial Vector within Mammalian Cells J774A1 cells, a murine macrophage cell line, were infected with strain SL7207[pAEN17], as described in Example 2. 4 hours after infection, different amounts of L-arabinose were added into individual wells of infected J774A1 cells up to a concentration in the medium of 4 mM, 40 mM and 400 mM, respectively. 3 hours after addition of L-arabinose cells were treated with 0.25% Triton X-100. Bacteria in the lysates were monitored for GFP expression by flow cytometry as described in Example 2. The analytical results are depicted in FIG. 7, with unspecific background fluorescence substracted.

It is seen that the fluorescence intensity of GFP increases with increasing concentrations of L-arabinose in the medium, demonstrating the gradual induction of the saccharide inducible promoter, leading to induction of plasmid replication and in turn to an increase in the synthesis of GFP due to elevated gene copy number.

These measurements demonstrate that the introduction of a bacterial vector into mammalian cells is obtained using the bacterial vector according to the invention, and induction of the synthesis of the replicase TrfA under the control of a saccharide inducible promoter by extracellular addition of the saccharide acting as its specific inductor substance leads to the amplification of the plasmid containing a constitutive expression cassette of the structural gene while contained in animal cells.

Example 6

In Vitro Induction of Lysis of Bacterial Vector within a Mammalian Organism

Figure 8:
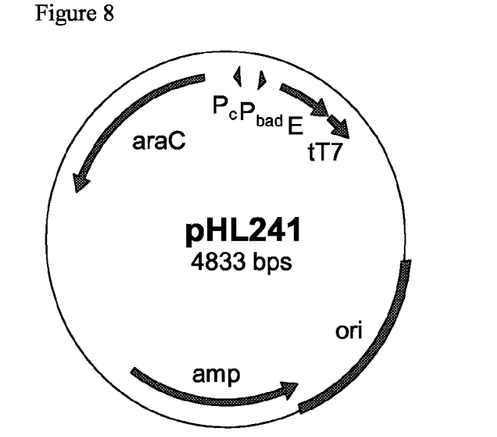

In order to demonstrate the lysis of bacterial vectors according to the invention, controllable by addition of the inductor saccharide for the saccharide inducible promoter, a plasmid according to FIG. 8 was constructed. This plasmid carries the lysis gene E of bacteriophage Φ X174 under the control of the saccharide inducible promoter $P_{BAD}$, demonstrating the strict regulation of $P_{BAD}$ in the non-induced state. The plasmid pHL241 shown in FIG. 8 was derived from plasmid pHL238 shown in FIG. 1 by exchanging gene gfp against gene E.

For infection, J774A1 cells were cultured and infected with SL7207 bearing the plasmid of FIG. 8 according to the procedure of Example 2. Induction was by addition of L-arabinose to the final concentrations in cell culture medium as given in FIG. 9, for an induction period of 3 hours. Following induction, cells were harvested and lysed by addition of Triton X-100 to a concentration of 1 g/L. For re-isolation, intracellular bacterial vectors were plated on LB-agar containing ampicillin for quantification of viable bacteria as colony forming units (CFU).

Figure 9:
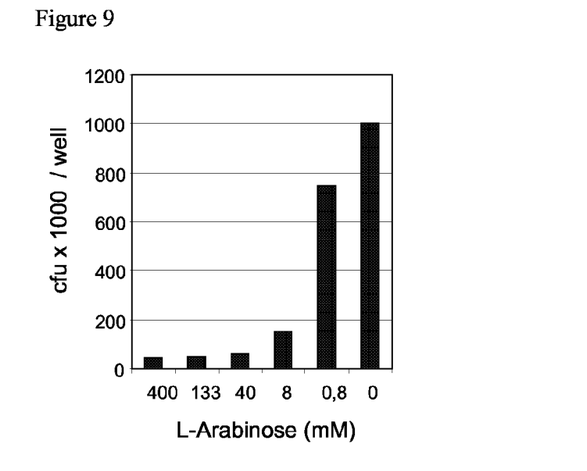

The results depicted in FIG. 9 show that presence of the inductor saccharide L-arabinose drastically decreases the number of viable bacterial vectors inside infected J774A1 cells. The number of viable bacteria which can be re-isolated from infected J774A1 cells is reduced by presence of L-arabinose as a result of lysis of the bacterial vector caused by synthesis of the gene E product.

This example shows the effectiveness of bacterial vectors according to the invention, based on attenuated invasive bacteria, containing a saccharide inducible promoter in combination with a suicide gene as a system for terminating the infection of mammalian cells with invasive attenuated bacteria by controlled lysis. This controlled termination of the infection inevitably leads to the release of the bacterial vector contents into the phagosome or cytosol of the infected cell, respectively.

Example 7

In Vivo Inducible Lysis of Bacterial Vectors within an Infected Mammalian Organism This example demonstrates the applicability of the attenuated invasive bacteria containing a saccharide inducible promoter controlling a suicide gene for terminating the infection of cells within a mammal, i.e. a mouse. The lysis gene E of bacteriophage ΦX174 was contained on the plasmid of FIG. 8, harboured within Salmonella strain SL7207. This bacterial vector was intravenously injected into Balb/c mice as described in Example 3. Two days after infection of mice, L-arabinose was injected intravenously in amounts of 60 mg, 8 mg and 1.6 mg per animal, saline solution was used as background control (0). Following 4 hours after induction, animals were sacrificed and the spleen was homogenized for determination of the number of viable bacterial vectors. Viable bacterial vectors were counted after plating according to Example 6.

Figure 10:
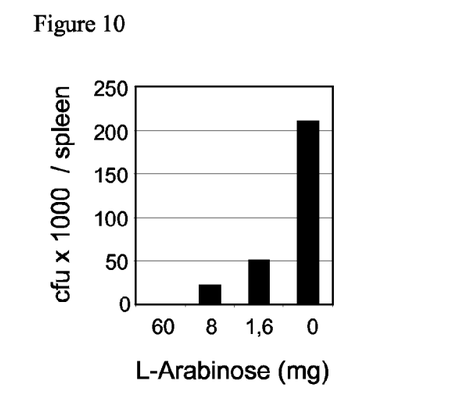
FIG. 10 shows the number of viable bacterial vector re-isolated from the spleen of a mouse infected with the Salmonella enterica serovar Typhimurium strain SL7207 bearing the plasmid according to FIG. 8 after administration of various amounts of L-arabinose FIG. 11 schematically shows a plasmid harbouring the luciferase gene (luc) as a transgene, FIG. 12 A shows colony forming units (cfu) re-isolated from the tissues indicated at time intervals (h) after administration of inductor saccharide to an animal containing bacterial vector comprising the plasmid according to FIG. 11, FIG. 12 B shows transgene activity (relative luminescence units, RLU) of the reporter gene in different tissue homogenates obtained from animals treated with bacterial vector and, subsequently, with inductor saccharide as for FIG. 12 A, FIG. 12 C shows transgene activity per bacterial vector (RLU/cfu) of the reporter gene in different tissue homogenates obtained from animals treated with bacterial vector and, subsequently, with inductor saccharide as for FIG. 12 A, FIGS. 13 A, B and C show cfu, RLU and relative RLU (RLU/cfu), respectively, for Peyer patches obtained from animals treated with bacterial vector of FIG. 12 A by oral administration and, subsequently, with inductor saccharide administered in solution as drinking water, FIG. 14 schematically shows a plasmid comprising a lysis gene as the transgene for Tn-7 mediated chromosomal integration into the bacterial vector's genome.

The results depicted in FIG. 10 demonstrate that the activity of the saccharide inducible promoter contained in attenuated invasive bacteria according to the invention can be induced in vivo by the systemic application of inductor substance. Injection of the inductor saccharide leads to the activation of the saccharide inducible promoter $P_{BAD}$, resulting in expression of gene E and, subsequently, in an efficient lysis of the bacterial vector. Results furthermore nicely demonstrate that the activity of the saccharide inducible promoter can be regulated in a gradual manner by variation of the saccharide concentration acting as the inductor.

FIGS. 9 and 10 further show that regulation of the toxic gene under the control of the saccharide inducible promoter is sufficiently tight to allow for the maintenance of the respective plasmid, encoding a toxic gene product, within bacterial vectors.

Example 8

In Vivo Induction of Transgene Activity from Bacterial Vector within a Tumor of an Animal This example demonstrates the use of a pharmaceutical combination of a bacterial vector with the inductor saccharide to induce a transgene activity within an animal, with preference to tumor tissue.

Figure 11:
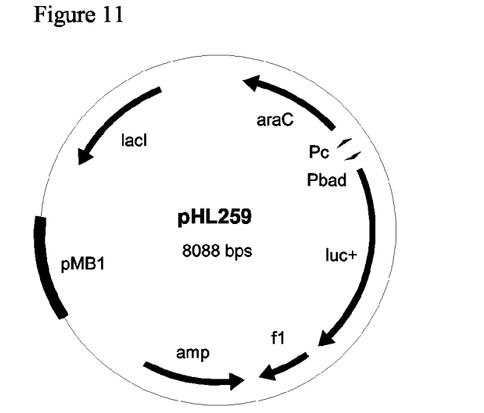

As a representative for a transgene, the luciferase gene from the firefly *Photinus pyralis* was used as the reporter gene. As the saccharide inducible promoter element, $P_{BAD}$ from the L-arabinose operon of *E. coli* was functionally linked to the luciferase gene, the promoter element further being in conjunction with the structural gene for its regulator protein araC under the control of its natural own promoter ($P_C$). The bacterial vector was generated by transforming *Salmonella enterica* serovar *Typhimurium*, vaccine strain SL7207, with the plasmid containing the transgene under the control of the saccharide inducible promoter by electroporation. This plasmid, termed pHL259 is schematically shown in FIG. 11.

As an example for an animal having a tumor, Balb/c mice were subcutaneously inoculated abdominally with $10^6$ cells of the colon adenocarcinoma cell line CT26. After this tumor generation treatment, mice bearing tumors of approximately 400-600 $mm^3$ were intravenously injected with $5 \times 10^6$ bacteria of the above bacterial vector (SL7207[pHL259]), representing the first component of the pharmaceutical combination, suspended in phosphate buffered saline (PBS). Three days post infection, L-arabinose as the appropriate inductor saccharide, representing the second component of the pharmaceutical combination, was administered intraperitoneally, dissolved in PBS. Subsequently, mice were sacrificed and the tumors, spleens and livers dissected, then transferred into 3 mL of sterile, ice-cold PBS containing 0.1% (vol/vol) Triton X-100.

In order to determine the distribution of the vector component within the animal organism as well as the induction of the transgene activity due to the administration of the second component, tumor tissue, spleens and livers were analysed.

Tissues were disrupted in a Polytron PG3000 homogenizer (Kinematica, Littau, Switzerland). Homogenates were diluted in PBS and streaked on medium plates with selective antibiotic (ampicillin). Colonies were counted after incubation of plates. As a result, the number of bacteria in respective tissues could be calculated by counting the resulting colony forming units (cfu) for each organ. The results are shown in FIG. 12A.

The induction of the transgene was determined by measurement of the reporter gene (luciferase) activity from tissue homogenates after dilution (1:1) in 2× luciferase assay lysis buffer (50 mM tris-HCl, 4 mM DTT, 20% (vol/vol) glycerol, 2% (vol/vol) Triton X-100, 2 mg/mL lysozyme, pH 8.3), incubation at 25° C. for 10 minutes, centrifugation at 3,000×g for 3 minutes, 10 μL supernatant were added to 100 mL LARII reagent of the luciferase assay system according to the manufacturer's instructions (Promega, Mannheim, Germany). Luminescence intensity was measured spectrometrically in a luminometer (Lumat LB9507, Berthold, Pforzheim, Germany). Dilution was taken into account when calculating RLU per organ.

Figure 12:
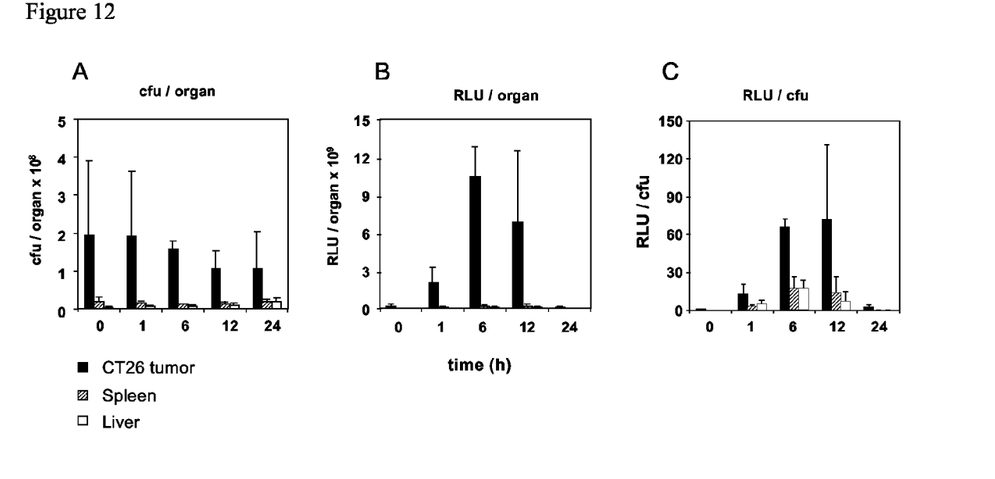

The transgene activity, represented by the luciferase activity (RLU) is shown in FIG. 12 B, and relative transgene activity is shown in FIG. 12 C, i.e. the relative luminescence per colony forming units (RLU/cfu).

For all animals, the number of bacteria found in tumors by far exceeded the number of bacteria detected in the spleen or liver, over the course of time. Here, the preference of the bacterial vector component for accumulation in tumor tissue can be seen.

As can be taken from FIGS. 12 B and 12 C, the administration of the second component, namely L-arabinose, induces transgene expression for all tissues tested. For the tissues tested here, absolute transgene activity was greatest in tumor tissue, with the main activity at about 6 hours past administration of the inductor saccharide. Note that transgene activity in spleen and liver was very low to about background levels, and even presence of the inductor saccharide did not cause significant activity levels.

Further, relative transgene activity, i.e. in relation to bacterial numbers in the tissues tested, as shown in FIG. 12 C, demonstrates that transgene activity was most effectively induced in tumor tissue, whereas spleen and liver show considerably lower levels of relative transgene expression at the intervals tested after administration of the inductor saccharide.

Further, this example demonstrates that transgene induction is transient and, accordingly, can be repeated by repetition of the administration of the inductor saccharide, and further demonstrates that transgene induction can be modulated by the amount of inductor saccharide and, i.e. transgene activity is inductor saccharide concentration dependent.

Example 9

In Vivo Induction of Transgene Activity from Bacterial Vector within a Mammal Using the Pharmaceutical Combination as a Vaccine Balb/c mice were orally inoculated with $5 \times 10^8$ cfu of recombinant strain SL7207[pHL259], which was obtained as described in Example 8. At day 6 after administration of the bacterial vector, mice were separated into groups, one group receiving drinking water containing 250 mg/mL L-arabinose for 24 hours as the inductor saccharide; a second group received drinking water, identically containing L-arabinose for 6 hours and a third group received a total of 120 mg L-arabinose, dissolved in PBS, intraperitoneally. 6 hours after administration of the inductor saccharide, mice were sacrificed and Peyer patches were isolated and homogenated.

Figure 13:
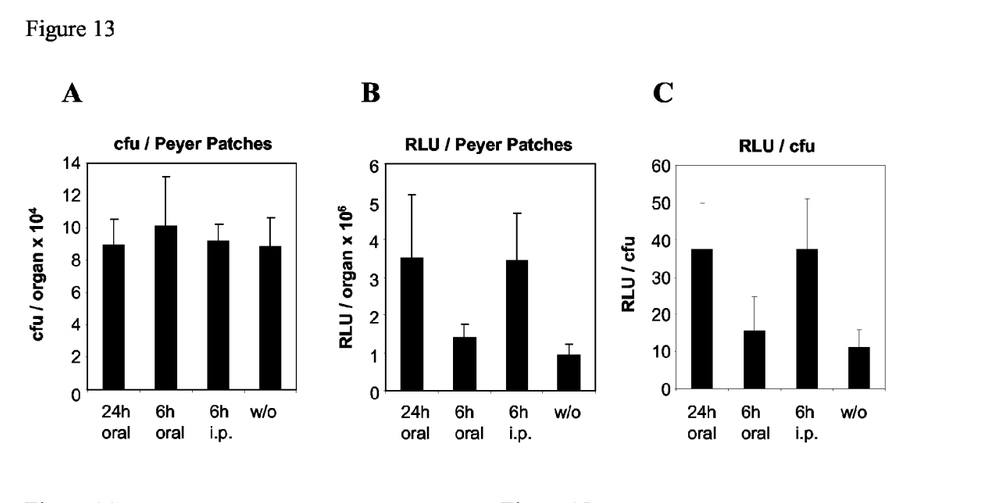

From homogenates of Peyer patches, bacterial numbers and transgene activity (luciferase) was determined as described in Example 8. Results are shown in FIGS. 13 A, 13 B, and 13 C, demonstrating that oral administration of the bacterial vector component, followed by oral administration of the inductor saccharide is sufficient to induce transgene expression in Peyer patches, representing an immune inductive site.

Example 10

Figure 14:
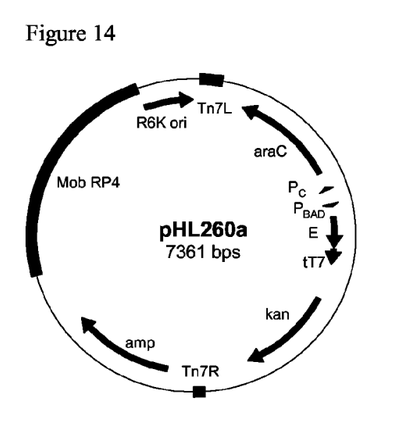

Use of a Pharmaceutical Composition for the Delivery of Nucleic Acid and/or Protein to Tumor Tissue within Animals As an example for a bacterial vector containing a transgene that can be activated to initiate lysis of the bacterial vector within an animal, strain SL7207 was genetically manipulated by integrating part of plasmid HL260a (schematically shown in FIG. 14) by Tn7 mini-transposon-mediated site specific integration into the bacterial chromosome, essentially according to Bao et al. (Gene 109, 167-168 (1991)), containing gene E of bacteriophage phiX174 under the control of the $P_{BAD}$ promoter.

Figure 15:
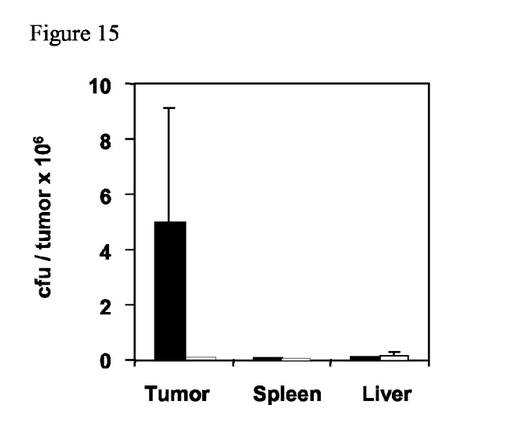
FIG. 15 shows cfu determined for indicated tissue homogenates obtained from an animal administered with a vector harbouring the lysis gene according to FIG. 14 and, subsequently, with inductor saccharide, FIGS. 16 A and B show cfu and transgene activity (RLU), respectively, determined in the tissues indicated of animals administered with bacterial vectors based on different bacteria, each harbouring the plasmid according to FIG. 11, after administration of inductor saccharide, and FIG. 17 schematically shows a bacterial vector, forming the first component of the pharmaceutical combination according to the invention.

As an example for animals, mice were used that had been implanted subcutaneously with a CT26 tumor as described in Example 8. As the first component of the pharmaceutical combination according to the invention, recombinant strain SL7207::HL260a, containing the Tn7 mediated chromosomally integrated copy of the transgene (gene E), was administered by intravenous injection ($5 \times 10^6$ bacteria in PBS). At 3 days subsequent to the administration of the bacterial vector, the second component, namely 120 mg L-arabinose dissolved in PBS, was administered by intraperitoneal injection, followed by an identical second injection 12 hours later. At 6 hours after the second administration of inductor saccharide, mice were sacrificed and their tumor tissue, spleens and livers isolated and homogenized as described in Example 8, including the determination of bacterial numbers from homogenates. Results are shown in FIG. 15, showing bacterial counts of animals having received mock inductor, namely PBS (black columns) and animals having received administration of the inductor saccharide (white columns), for tumor tissue, spleen and liver, respectively. These results demonstrate that administration of the inductor saccharide lead to lysis of the bacterial vector, especially in tumor tissue, where bacterial vector had predominantly localized and/or increased in number, at least in relation to spleen and liver.

This example demonstrates that a lysis gene as a transgene may be used for liberation of bacterial vector's contents, e.g. nucleic acid, protein, for delivery to tissue within an animal, controlled by administration of the second component of the pharmaceutical combination. Further, a lysis gene as a transgene may be used for a drastic reduction of bacterial vector concentration, even in most intensely populated tissue, e.g. tumor tissue. In this respect, repeated lysis of the bacterial vector by repeated administration of the inductor saccharide is feasible, as concentrations of inductor saccharide can be adjusted to avoid lysis of the complete number of bacterial vector, i.e. leave some bacterial vectors for repopulation of tissue, again, predominantly of tumor tissue.

Example 11

Genetic Manipulation of Bacterial Vector Component to Enhance Transgene Activity The bacterial vector obtained in Example 10 was modified in a first alternative by T7-mediated chromosomal integration of a mini-transposon comprising the mutant lacY gene and, in a second alternative, by inactivating the ara operon by site-directed insertional mutagenesis.

When using the alternatively manipulated vectors for the tumor treatment in mice according to Example 10, both vector alternatives demonstrate a similar colonization of tumor tissue in combination with an enhancement of reduction in residual vector counts following administration of the inductor saccharide, i.e. increased efficiency in transgene activity induction.

Example 12

Comparison of Different Bacteria for Generating the Bacterial Vector Component in Relation to the Efficiency in Colonizing a Tumor of an Animal For an evaluation of the suitability of bacteria for generating the bacterial vector component for use in the pharmaceutical composition according to the invention, the E. coli S1laboratory strain Top10 (Invitrogen, Karlsruhe, Germany), Salmonella enterica serovar Typhimurium SL7207 (SL7207, described by Hoiseth et al., Nature 291 238-239 (1981)), and Salmonella enterica strains Salmoporc and Suisaloral (IDT, Roβlau, Germany) were transformed by electroporation with plasmid pHL259, encoding luciferase as a reporter gene.

Mice bearing CT26 tumors as described in Example 8 were administered the bacterial vector by subcutaneous injection ($5 \times 10^6$ bacteria) in PBS. 3 days later, the inductor saccharide (120 mg L-arabinose in PBS) was administered by intraperitoneal injection. 6 hours later, mice were sacrificed and tumor tissue, spleen and liver removed and analyzed for bacterial vector content and transgene activity after homogenization according to Example 8.

Figure 16:
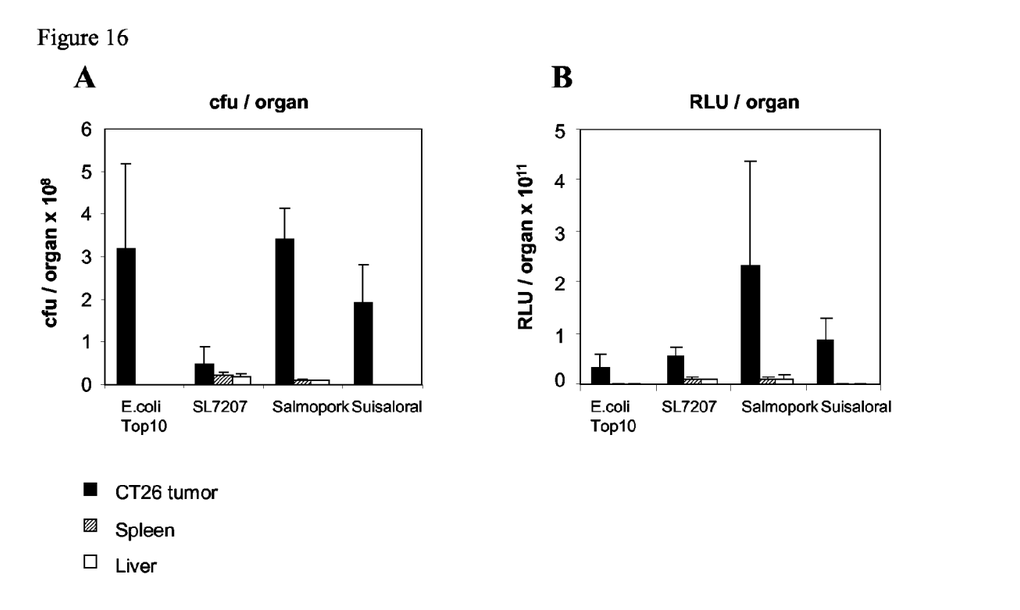

The results obtained for the different bacterial vectors under otherwise identical conditions are shown in FIGS. 16A and B for efficiency in colonizing the tissue (cfu) and efficiency of transgene activity (RLU), respectively. The results show that different bacterial strains can be used to generate the bacterial vector component of the pharmaceutical combination according to the invention, yielding variations in the efficiency of colonization (cfu) of tumor tissue in relation to spleen and liver, as well as different efficiencies in transgene activity (RLU) in tumor tissue in relation to spleen and liver.

It can be seen that all bacterial vectors predominantly colonized tumor tissue, although with differing efficiency. Administration of inductor saccharide caused transgene activity, again predominantly confined to tumor tissue. However, efficiency of colonization of tumor tissue was not correlated to transgene activation for all vectors.

When monitoring the general health status of the animals tested, it was found that the bacterial vector based on E. coli Top10 caused the least pronounced impairment.

Accordingly, the present invention provides a choice of vectors for use in the pharmaceutical combination of components to select a bacterial vector which predominantly accumulates in tumor tissue, and the transgene activity can be regulated by administration of the inductor saccharide, depending inter alia on the bacterium the vector is based on.

Further, this example provides an assay for identification of bacteria suitable for generating the bacterial vector component of the invention, using re-isolation of bacteria from tissue samples of an animal having received the bacterial vector component for assessing the efficiency of colonization of different tissue, and a reporter gene for assessing induction of transgene activity by subsequent administration of the inductor saccharide component.

Example 13

Figure 17:
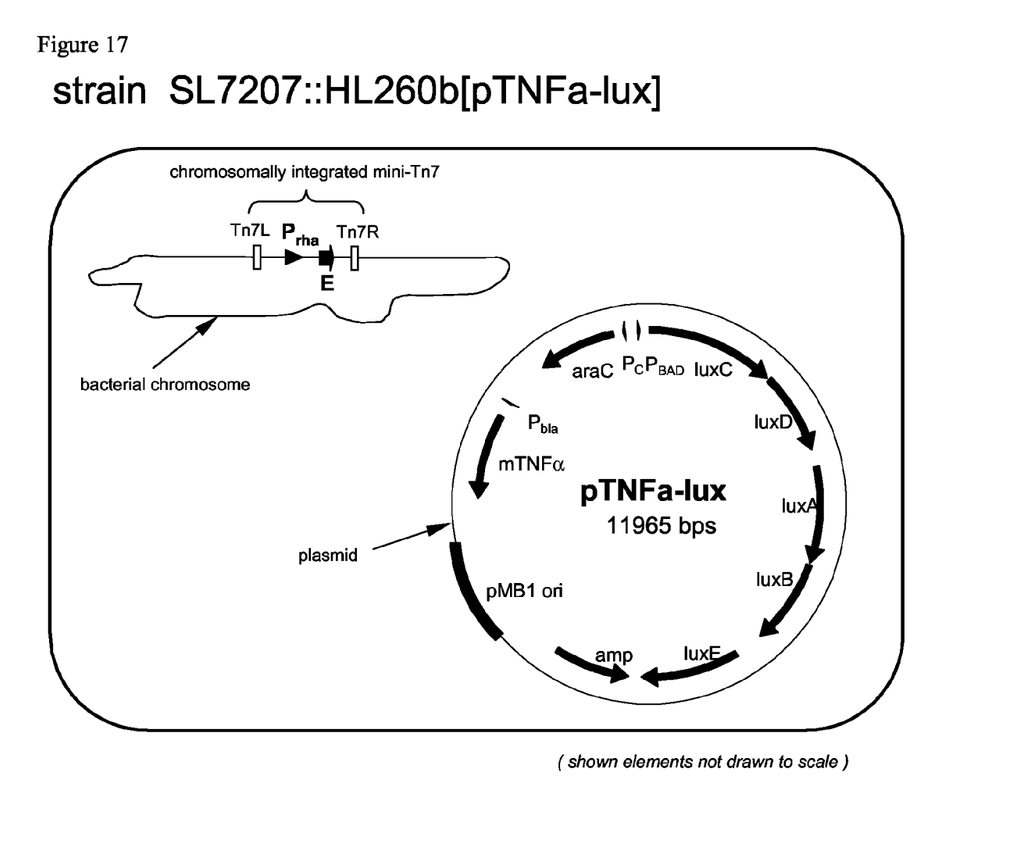

Bacterial Vector Comprising a Combination of Transgenes, Each Under the Control of a Different Saccharide Inducible Promoter As an example for multifunctional bacterial vectors for use in the pharmaceutical combination according to the invention, vaccine strain SL7207 was genetically manipulated by Tn7 mediated chromosomal integration of the mini-transposon of a plasmid pHL260b, modified from pHL260a by replacing the $P_{BAD}$ promoter by the L-rhamnose inducible promoter ($P_{rha}$), derived from plasmid pJOE2702 (Stumpp et al., Biospektrum 6, 33-36(2000)). This strain chromosomally contains at least one copy of gene E of bacteriophage phiX174 under the control of the rhamnose inducible promoter ($P_{rha}$). The resultant strain was then transformed with plasmid pTNFa-lux, containing the bioluminescence operon of *Photorhabdus luminescence* under control of the $P_{BAD}$ promoter in combination with the mouse TNFalpha gene under the control of the constitutive promoter from beta-lactamase ($P_{bla}$). The resultant bacterial vector is schematically shown in FIG. 17.

As described in Example 8, Balb/c mice bearing a CT26 tumor were administered 5×10$^6$ bacterial vector, suspended in PBS by intravenous administration. 3 days after this administration, the inductor saccharide, namely 120 mg L-rhamnose, dissolved in PBS, was administered intraperitoneally. As a result, lysis of bacterial vector and release of TNFalpha was observed. Upon administration of 120 mg L-arabinose dissolved in PBS intraperitoneally, to the same mice 1 day later, as well as on consecutive days, colonization of tumor tissue by bacterial vectors was monitored by spectrometry, more specifically luminometric analysis of anesthesized mice using a CCD camera.

It could be shown that repeated administration of the inductor saccharides L-rhamnose and, subsequently, of L-arabinose, results in bacterial lysis and release of TNFalpha in combination with bioluminescence (RLU). Further, monitoring of tumor location and size could be demonstrated by luminometric analysis of a monitoring transgene product, exemplified here by bioluminescence operon of *Photorhabdus luminescence*, also allowing observation of the effects of administration of inductor saccharide inducing the therapeutic transgene, exemplified here by TNFalpha.

This example demonstrates that different transgene activities can be induced independently and repeatedly at the site of localization of the bacterial vector, exemplified here by tumor tissue.

The invention claimed is:

1. A method of administering a system of pharmaceuticals comprising:
   administration to an animal or a human patient of a bacterial vector, the bacterial vector being a recombinant non-invasive or invasive bacterium which has been genetically modified to contain a transgene functionally linked to a saccharide inducible promoter, and
   subsequent administration of an inductor saccharide to the patient that has previously received the bacterial vector.

2. The method of claim 1 wherein the bacterial vector is administered in a way selected from the group consisting of systemically, nasally, orally, rectally or otherwise mucosally.

3. The method of claim 1 wherein the saccharide inductor is administered independently from the localization that the bacterial vector has reached.

4. The method of claim 1 wherein the bacterial vector is based on bacteria selected from the group consisting of attenuated bacteria which are invasive to animal cells and bacteria commensal to animal cells or to animals.

5. The method of claim 1 wherein the saccharide inducible promoter and the inductor saccharide are selected from combinations consisting of the arabinose promoter and L-arabinose, the rhamnose promoter and rhamnose, and the xylulose promoter and xylulose.

6. The method of claim 1 wherein the saccharide inducible promoter is the regulatory module of a bacterial L-arabinose operon.

7. The method of claim 6 wherein the bacterial L-arabinose operon originates from *E. coli*.

8. The method of claim 1 wherein the transgene encodes a structural protein or a reactive RNA species.

9. The method of claim 1 wherein the transgene encodes synthetic pathway enzymes for the synthesis of biologically or pharmaceutically active effector molecules.

10. The method of claim 1 wherein the transgene encodes a peptide catalyzing the conversion of a pro-drug to a drug.

11. The method of claim 1 wherein the transgene encodes the product of a suicide gene.

12. The method of claim 11 wherein the suicide gene is selected from the group consisting of bacteriotoxic and bacteriolytic genes.

13. The method of claim 1 wherein the bacterial vector is genetically manipulated to express a heterologous inductor saccharide transporter system or a mutant inductor saccharide transporter system.

14. The method of claim 1 wherein the bacterial vector is genetically manipulated to express its intrinsic inductor saccharide transporter system at increased levels.

15. The method of claim 1 wherein the bacterial vector is genetically manipulated by inactivation of the metabolic pathway of the inductor saccharide.

16. The method of claim 1 wherein the bacterial vector is genetically manipulated to contain a heterologous secretion system.

17. The method of claim 1 wherein the transgene encodes a signal sequence of a secretion system.

18. The method of claim 1 wherein the medical treatment is administration of a vaccine.

19. The method of claim 1 wherein the medical treatment is treatment for tumors.

20. The method of claim 1 wherein the medical treatment is treatment for probiotics or functional food.

21. The method of claim 1 wherein the inductor saccharide is a saccharide analogon.

22. The method of claim 1 wherein the transgene comprises a coding sequence selected from the group consisting of sequences encoding synthetic pathway enzymes for the production of an immunomodulating compound or a toxic compound, or sequences encoding an antibody, a heterologous peptide, or a self-antigen.

23. The method of claim 1 wherein the transgene comprises a monitoring transgene.

24. The method of claim 23 wherein the medical treatment is monitoring of tumor tissue by spectroscopy or luminometric analysis.

* * * * *

UNITED STATES PATENT AND TRADEMARK OFFICE
CERTIFICATE OF CORRECTION

PATENT NO. : 8,093,025 B2  Page 1 of 1
APPLICATION NO. : 11/667034
DATED : January 10, 2012
INVENTOR(S) : Holger Loessner et al.

It is certified that error appears in the above-identified patent and that said Letters Patent is hereby corrected as shown below:

In the Specification:

Col. 9, line 59    Before "to create" please insert --one--.

Col. 15, line 33   After "secretion system, which" please insert --can--.

Col. 17, line 66   Before "the results" please insert --shows--.

Signed and Sealed this
First Day of October, 2013

Teresa Stanek Rea
*Deputy Director of the United States Patent and Trademark Office*